(12) United States Patent
Iwasaki et al.

(10) Patent No.: US 8,741,512 B2
(45) Date of Patent: Jun. 3, 2014

(54) ADDITIVE FOR ELECTROPHOTOGRAPHIC PHOTORECEPTOR, ELECTROPHOTOGRAPHIC PHOTORECEPTOR, PROCESS CARTRIDGE, AND IMAGE FORMING APPARATUS

(75) Inventors: Masahiro Iwasaki, Kanagawa (JP); Yuko Yamano, Kanagawa (JP); Yukimi Kawabata, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 29 days.

(21) Appl. No.: 13/612,153

(22) Filed: Sep. 12, 2012

(65) Prior Publication Data

US 2013/0252150 A1  Sep. 26, 2013

(30) Foreign Application Priority Data

Mar. 23, 2012  (JP) ................................ 2012-068297

(51) Int. Cl.
*G03G 5/04*  (2006.01)

(52) U.S. Cl.
USPC ..................... 430/58.65; 430/58.75; 430/58.8

(58) Field of Classification Search
USPC .................. 430/58.65, 58.75, 58.8
See application file for complete search history.

(56) References Cited

U.S. PATENT DOCUMENTS

| | | | |
|---|---|---|---|
| 5,160,487 A | 11/1992 | Morishita et al. | |
| 5,352,834 A | 10/1994 | Morishita et al. | |
| 5,403,958 A | 4/1995 | Morishita et al. | |

FOREIGN PATENT DOCUMENTS

| | | |
|---|---|---|
| JP | A-05-006010 | 1/1993 |
| JP | A-06-025120 | 2/1994 |
| JP | A-07-126224 | 5/1995 |
| JP | A-11-218945 | 8/1999 |
| JP | A-2005-156742 | 6/2005 |

*Primary Examiner* — Hoa V Le
(74) *Attorney, Agent, or Firm* — Oliff PLC

(57) ABSTRACT

Provided is an additive for an electrophotographic photoreceptor which is represented by Formula (I):

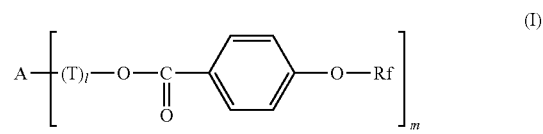

wherein, A represents an m-valent organic group derived from arylamine represented by Formula (II) or Formula (III); T represents a divalent hydrocarbon group having from 1 to 10 carbon atoms; Rf represents a branched hydrocarbon group having from 3 to 10 carbon atoms in which at least one hydrogen atom is substituted with a fluorine atom; l represents 0 or 1; and m represents an integer of 1 to 4:

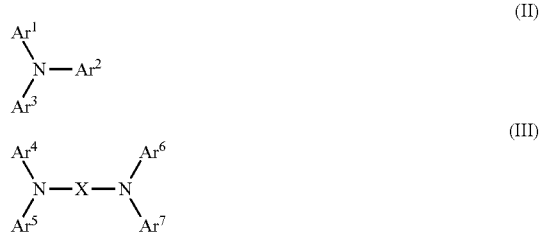

wherein, $Ar^1$, $Ar^2$, and $Ar^3$ each independently represent a substituted or unsubstituted aryl group having from 6 to 20

Wavenumber [cm-1]

carbon atoms; $Ar^4$, $Ar^5$, $Ar^6$, and $Ar^7$ each independently represent a substituted or unsubstituted aryl group having from 6 to 20 carbon atoms; and X represents a divalent organic group represented by Formula (IV), Formula (V), or Formula (VI):
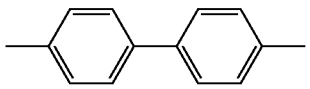
(IV)
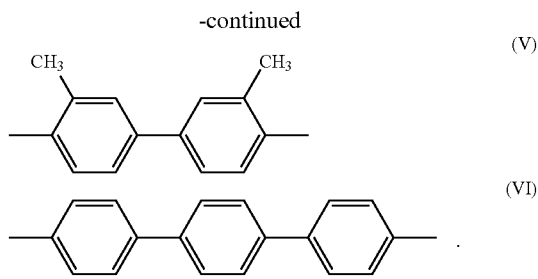
17 Claims, 7 Drawing Sheets

ADDITIVE FOR ELECTROPHOTOGRAPHIC PHOTORECEPTOR, ELECTROPHOTOGRAPHIC PHOTORECEPTOR, PROCESS CARTRIDGE, AND IMAGE FORMING APPARATUS

CROSS-REFERENCE TO RELATED APPLICATIONS

This application is based on and claims priority under 35 USC 119 from Japanese Patent Application No. 2012-068297 filed Mar. 23, 2012.

BACKGROUND

1. Technical Field

The present invention relates to an additive for an electrophotographic photoreceptor, an electrophotographic photoreceptor, a process cartridge, and an image forming apparatus.

2. Related Art

In the related art, various compounds are known as a photoconductive material and electrophotographic photoreceptors including the same are also known.

SUMMARY

According to an aspect of the invention, there is provided an additive for an electrophotographic photoreceptor which is represented by Formula (I):

$$A - \left[ (T)_l - O - \underset{\underset{O}{\|}}{C} - \text{(phenylene)} - O - Rf \right]_m \quad (I)$$

wherein in Formula (I), A represents an m-valent organic group derived from arylamine represented by Formula (II) or Formula (III); T represents a divalent hydrocarbon group having from 1 to 10 carbon atoms; Rf represents a branched hydrocarbon group having from 3 to 10 carbon atoms in which at least one hydrogen atom is substituted with a fluorine atom; l represents 0 or 1; and m represents an integer of 1 to 4;

$$\underset{Ar^3}{\overset{Ar^1}{\diagdown}} N - Ar^2 \quad (II)$$

$$\underset{Ar^5}{\overset{Ar^4}{\diagdown}} N - X - N \underset{Ar^7}{\overset{Ar^6}{\diagup}} \quad (III)$$

wherein in Formula (II), $Ar^1$, $Ar^2$, and $Ar^3$ each independently represent a substituted or unsubstituted aryl group having from 6 to 20 carbon atoms; in Formula (III), $Ar^4$, $Ar^5$, $Ar^6$, and $Ar^7$ each independently represent a substituted or unsubstituted aryl group having from 6 to 20 carbon atoms; and X represents a divalent organic group represented by Formula (IV), Formula (V), or Formula (VI):

$$-\text{(biphenyl)}- \quad (IV)$$

$$-\text{(dimethylbiphenyl with CH}_3\text{ groups)}- \quad (V)$$

$$-\text{(terphenyl)}- \quad (VI)$$

BRIEF DESCRIPTION OF THE DRAWINGS

Exemplary embodiments of the present invention will be described in detail based on the following figures, wherein.

DETAILED DESCRIPTION

Figure 1:
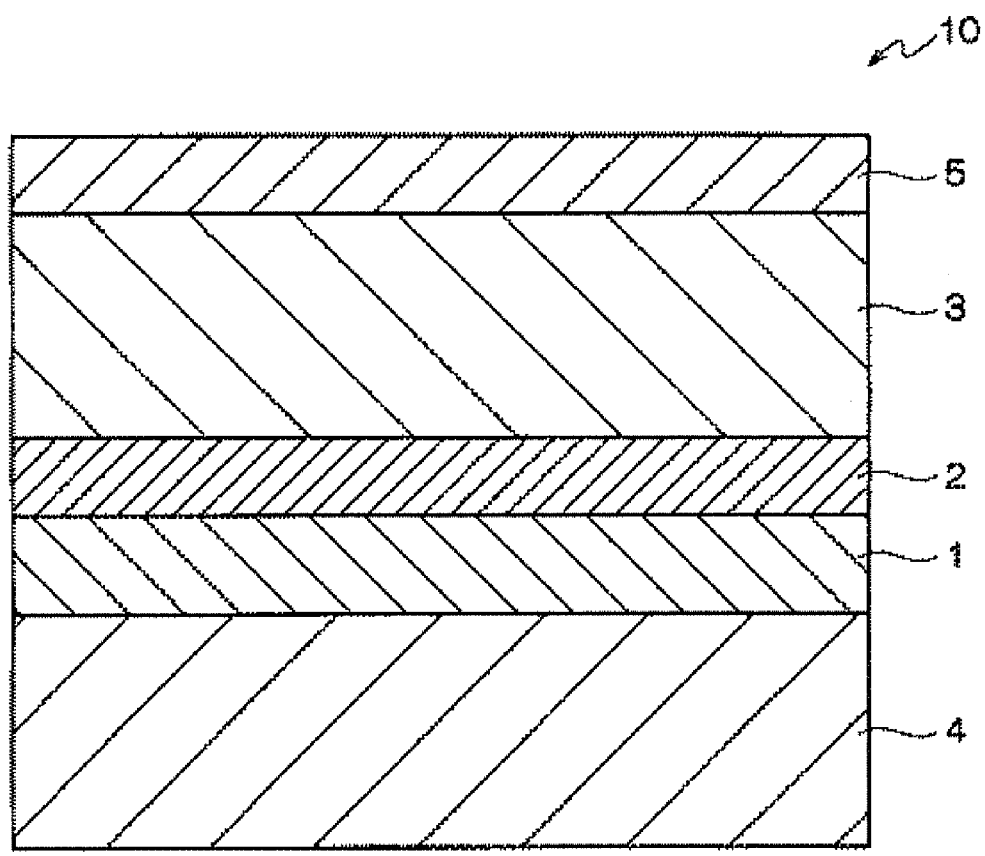
FIG. 1 is a cross-sectional view schematically illustrating a part of an electrophotographic photoreceptor according to an exemplary embodiment of the invention.

Hereinafter, an additive for an electrophotographic photoreceptor, an electrophotographic photoreceptor, a process cartridge, and an image forming apparatus according to exemplary embodiments of the invention will be described in detail.

Additive for Electrophotographic Photoreceptor

The additive for an electrophotographic photoreceptor according to the exemplary embodiment is a compound represented by Formula (I) below.

$$A - \left[ (T)_l - O - \underset{\underset{O}{\|}}{C} - \text{(phenylene)} - O - Rf \right]_m \quad (I)$$

In Formula (I), A represents an m-valent organic group derived from arylamine represented by Formula (II) or Formula (III); T represents a divalent hydrocarbon group having from 1 to 10 carbon atoms; Rf represents a branched hydrocarbon group having from 3 to 10 carbon atoms in which at least one hydrogen atom is substituted with a fluorine atom; l represents 0 or 1; and m represents an integer of 1 to 4.

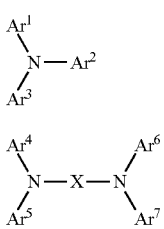 (II)

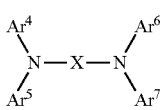 (III)

In Formula (II), $Ar^1$, $Ar^2$, and $Ar^3$ each independently represent a substituted or unsubstituted aryl group having from 6 to 20 carbon atoms.

In Formula (III), $Ar^4$, $Ar^5$, $Ar^6$, and $Ar^7$ each independently represent a substituted or unsubstituted aryl group having from 6 to 20 carbon atoms; and X represents a divalent organic group represented by Formula (IV), Formula (V), or Formula (VI) below.

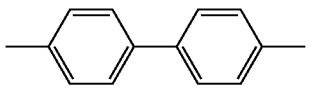 (IV)

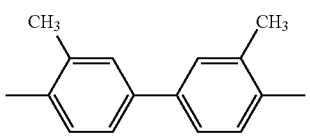 (V)

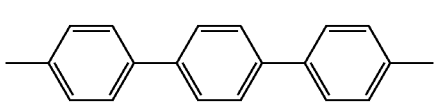 (VI)

The additive for an electrophotographic photoreceptor according to the exemplary embodiment is a compound represented by Formula (I) and has a structure in which 1 to 4 branched fluorinated hydrocarbon groups having from 3 to 10 carbon atoms are bonded to organic groups (charge transport structures) derived from a compound having a charge transport function, through a group (—O—C(=O)—$C_6H_4$—O—) derived from hydroxybenzoic acid ester or through a group derived from hydroxybenzoic acid ester and a divalent hydrocarbon group having from 1 to 10 carbon atoms.

According to the exemplary embodiment, an additive for an electrophotographic photoreceptor which suppresses the change of the electrical characteristics of an electrophotographic photoreceptor can be provided.

The reason is not clear but considered to be as follows.

In the additive for an electrophotographic photoreceptor according to the exemplary embodiment, it is considered that, by using 1 to 4 branched fluorinated hydrocarbon groups having from 3 to 10 carbon atoms, an effect of dispersing fluororesin particles is superior.

Therefore, when a composition for forming the outermost surface layer of an electrophotographic photoreceptor includes fluororesin particles and the additive for an electrophotographic photoreceptor according to the exemplary embodiment, it is considered that, even when the amount of a dispersing aid used for fluororesin particles is reduced, the composition has a superior dispersibility for the fluororesin particles. In many cases, as the dispersing aid used for fluororesin particles, a comb-shaped polymer having a perfluoroalkyl group in a side chain thereof is used. However, this compound is likely to cause a residual potential of a photosensitive layer to rise and charging stability to deteriorate. Therefore, by using the additive for an electrophotographic photoreceptor according to the exemplary embodiment, the amount of the compound used for forming the outermost surface layer may be reduced.

In addition, since the additive for an electrophotographic photoreceptor according to the exemplary embodiment has a structure only having the fluorinated hydrocarbon group, the charge transport structure, and the specific linking group, it is considered that, when the additive for an electrophotographic photoreceptor according to the exemplary embodiment is applied to the outermost surface layer of an electrophotographic photoreceptor, there is little adverse effect on the electrical characteristics of the outermost surface layer.

It is considered from the above description that the outermost surface layer of an electrophotographic photoreceptor, which is formed using a composition containing a charge transport material, fluororesin particles, and the additive for an electrophotographic photoreceptor according to the exemplary embodiment, has superior charging stability and little change in electrical characteristics after its use.

As a result, it is considered that an image forming apparatus including the above-described electrophotographic photoreceptor suppresses image defects such as unevenness in image density and graininess which are caused by the change of the electrical characteristics of an electrophotographic photoreceptor.

In addition, in a case where fluororesin particles as a composition for forming the outermost surface layer of an electrophotographic photoreceptor are dispersed in a curable resin, it is considered that, when the additive for an electrophotographic photoreceptor according to the exemplary embodiment is used in combination, in an electrophotographic photoreceptor which is formed using this composition, there are few aggregates of the fluororesin particles which are generated by volume shrinkage caused when the curable resin is cured. The aggregates of the fluororesin particles lead to toner filming when an electrophotographic photoreceptor is used over a long period of time. However, it is considered that, in the outermost surface layer of an electrophotographic photoreceptor which is formed using the above-described composition, toner filming rarely occurs; and as a result, even when the electrophotographic photoreceptor is used over a long period of time, image defects are suppressed.

In addition, when a binder resin is added to a composition for forming the outermost surface layer of an electrophotographic photoreceptor, it is considered that the additive for an electrophotographic photoreceptor according to the exemplary embodiment is easily soluble in the binder resin (which is selected in consideration of solubility in a charge transport material used in combination).

As a result, it is considered that the outermost surface layer of an electrophotographic photoreceptor, which is formed using a composition containing a binder resin and the additive for an electrophotographic photoreceptor according to the exemplary embodiment, has superior charging stability and little change in electrical characteristics after its use.

Furthermore, it is considered that the additive for an electrophotographic photoreceptor according to the exemplary embodiment includes 1 to 4 branched fluorinated hydrocarbon groups having from 3 to 10 carbon atoms; and as a result, the outermost surface layer of an electrophotographic photoreceptor, which is formed using a composition containing the additive for an electrophotographic photoreceptor according to the exemplary embodiment, has a superior release property, lubricity, and cleaning property even when the composition does not contain fluororesin particles. That is, the additive for an electrophotographic photoreceptor according to the exemplary embodiment may be used as a material which imparts a release property or lubricity to the outermost surface layer of an electrophotographic photoreceptor. In addition, it is considered that, due to its structure, the additive for an electrophotographic photoreceptor according to the exemplary embodiment has less bleeding as compared to the case of silicone oil or the like which is used in the related art in order to impart a release property or lubricity to a photosensitive layer of an electrophotographic photoreceptor.

Furthermore, it is considered that the additive for an electrophotographic photoreceptor according to the exemplary embodiment is a compound having a charge transport structure and thus has a function as a charge transport material. Therefore, when being included in a photosensitive layer of an electrophotographic photoreceptor, the additive for an electrophotographic photoreceptor according to the exemplary embodiment may be used as a charge transport material.

Hereinafter, a structure of the compound represented by Formula (I), which is the additive for an electrophotographic photoreceptor according to the exemplary embodiment, will be described in detail.

In Formula (I), A represents an m-valent organic group derived from arylamine represented by Formula (II) or Formula (III).

In Formula (II) and Formula (III), the substituted or unsubstituted aryl groups having from 6 to 20 carbon atoms which are represented by $Ar^1$, $Ar^2$, $Ar^3$, $Ar^4$, $Ar^5$, $Ar^6$ and $Ar^7$ are, for example, substituted or unsubstituted aryl groups having the following structures.

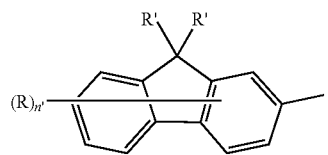
(Ar-1)

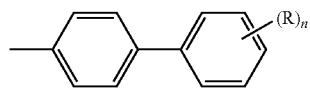
(Ar-2)

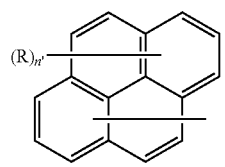
(Ar-3)

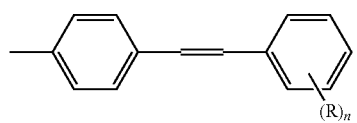
(Ar-4)

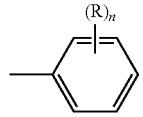
(Ar-5)

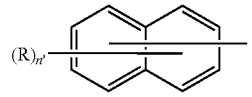
(Ar-6)

In the above structural formulae, R and R' each independently represent a halogen atom, a substituted or unsubstituted alkyl group having from 1 to 5 carbon atoms, a substituted or unsubstituted alkoxy group having from 1 to 5 carbon atoms, a substituted or unsubstituted hydroxyalkyl group having from 1 to 5 carbon atoms, a substituted or unsubstituted alkenyl group having from 2 to 5 carbon atoms, or a substituted or unsubstituted aryl group having from 6 to 14 carbon atoms. n represents an integer of 0 to 5, n' represents an integer of 0 to 7. R and R' each independently may be substituted with one or plural benzene rings.

It is preferable that the compound represented by Formula (II) be a compound represented by Formula (II-1).

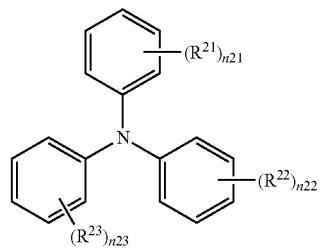
(II-1)

In Formula (II-1), $R^{21}$, $R^{22}$ and $R^{23}$ each independently represent a halogen atom, a substituted or unsubstituted alkyl group having from 1 to 5 carbon atoms, a substituted or unsubstituted alkoxy group having from 1 to 5 carbon atoms, a substituted or unsubstituted hydroxyalkyl group having from 1 to 5 carbon atoms, a substituted or unsubstituted alkenyl group having from 2 to 5 carbon atoms, or a substituted or unsubstituted aryl group having from 6 to 14 carbon atoms; and n21, n22, and n23 each independently represent an integer of 0 to 5.

When n21 is 2 or more, "$R^{21}$"s may be the same as or different from each other. When n22 is 2 or more, "$R^{22}$"s may be the same as or different from each other. When n23 is 2 or more, "$R^{23}$"s may be the same as or different from each other.

When the alkyl group, the alkoxy group, the hydroxyalkyl group, the alkenyl group, or the aryl group represented by $R^{21}$, $R^{22}$, and $R^{23}$ is substituted, examples of a substituent include halogen atoms (for example, fluorine, chlorine, bromine, and iodine); phenyl groups; and groups in which a hydrogen atom is excluded from a polycyclic aromatic hydrocarbon such as naphthalene, azulene, phenalene, phenanthrene, anthracene, triphenylene, pyrene, chrysene, or tetracene.

In Formula (III), among the divalent organic groups represented by Formulae (IV), (V), and (VI), it is preferable that X represent a divalent organic group represented by Formula (IV) or Formula (V).

It is preferable that the compound represented by Formula (III) be a compound represented by Formula (III-1) below.

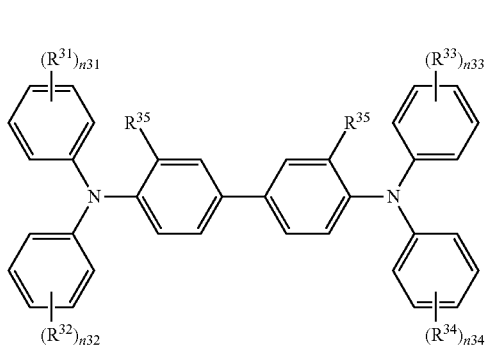
(III-1)

In Formula (III-1), $R^{31}$, $R^{32}$, $R^{33}$, and $R^{34}$ each independently represent a halogen atom, a substituted or unsubstituted alkyl group having from 1 to 5 carbon atoms, a substituted or unsubstituted alkoxy group having from 1 to 5 carbon atoms, a substituted or unsubstituted hydroxyalkyl group having from 1 to 5 carbon atoms, a substituted or unsubstituted alkenyl group having from 2 to 5 carbon atoms, or a substituted or unsubstituted aryl group having from 6 to 14 carbon atoms; n31, n32, n33, and n34 each independently represent an integer of 0 to 5; and $R^{35}$ represents a hydrogen atom or a methyl group.

When n31 is 2 or more, "$R^{31}$"s may be the same as or different from each other. When n32 is 2 or more, "$R^{32}$"s may be the same as or different from each other. When n33 is 2 or more, "$R^{33}$"s may be the same as or different from each other. When n34 is 2 or more, "$R^{34}$"s may be the same as or different from each other.

When the alkyl group, the alkoxy group, the hydroxyalkyl group, the alkenyl group, or the aryl group represented by $R^{31}$, $R^{32}$, $R^{33}$, and $R^{34}$ is substituted, examples of a substituent include halogen atoms (for example, fluorine, chlorine, bromine, and iodine); phenyl groups; and groups in which a hydrogen atom is excluded from a polycyclic aromatic hydrocarbon such as naphthalene, azulene, phenalene, phenanthrene, anthracene, triphenylene, pyrene, chrysene, or tetracene.

$R^{35}$ represents a hydrogen atom or a methyl group and preferably a hydrogen atom.

In Formula (I), T represents a divalent hydrocarbon group having from 1 to 10 carbon atoms. Examples of the divalent hydrocarbon group having from 1 to 10 carbon atoms represented by T include hydrocarbon groups having the following structures.

 (T-1)

 (T-2)

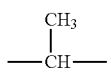 (T-3)

 (T-4)

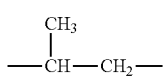 (T-5)

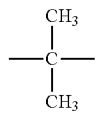 (T-6)

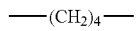 (T-7)

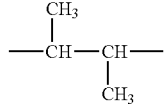 (T-8)

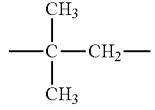 (T-9)

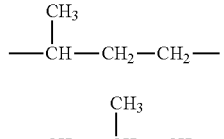 (T-10)

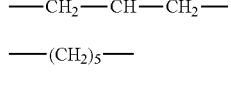 (T-11)

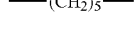 (T-12)

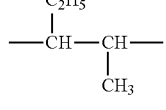 (T-13)

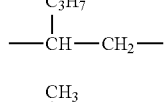 (T-14)

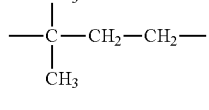 (T-15)

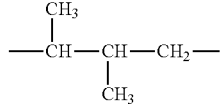 (T-16)

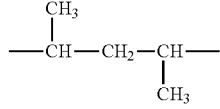 (T-17)

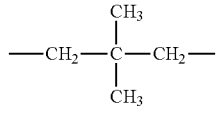 (T-18)

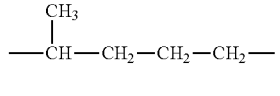 (T-19)

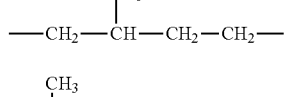 (T-20)

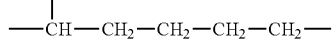 (T-21)

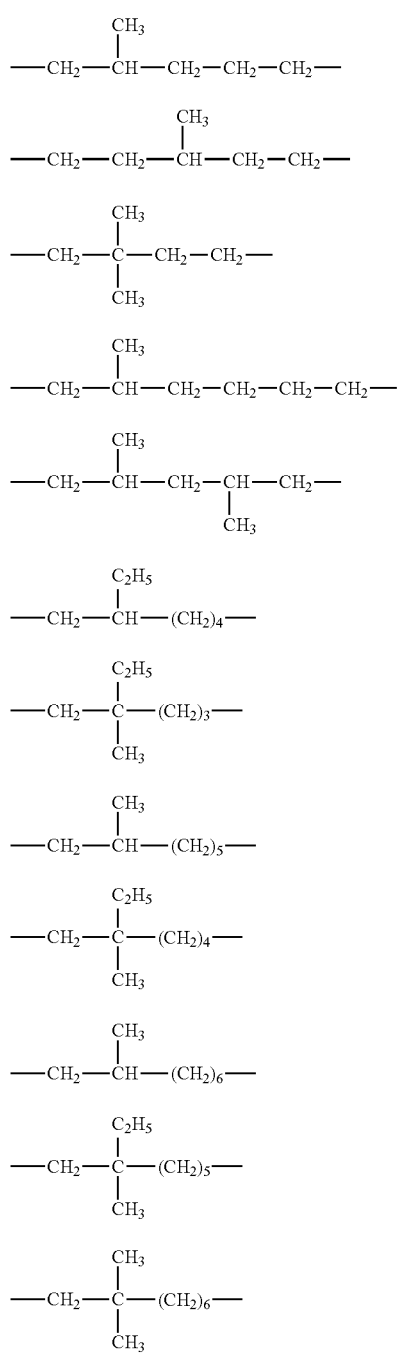

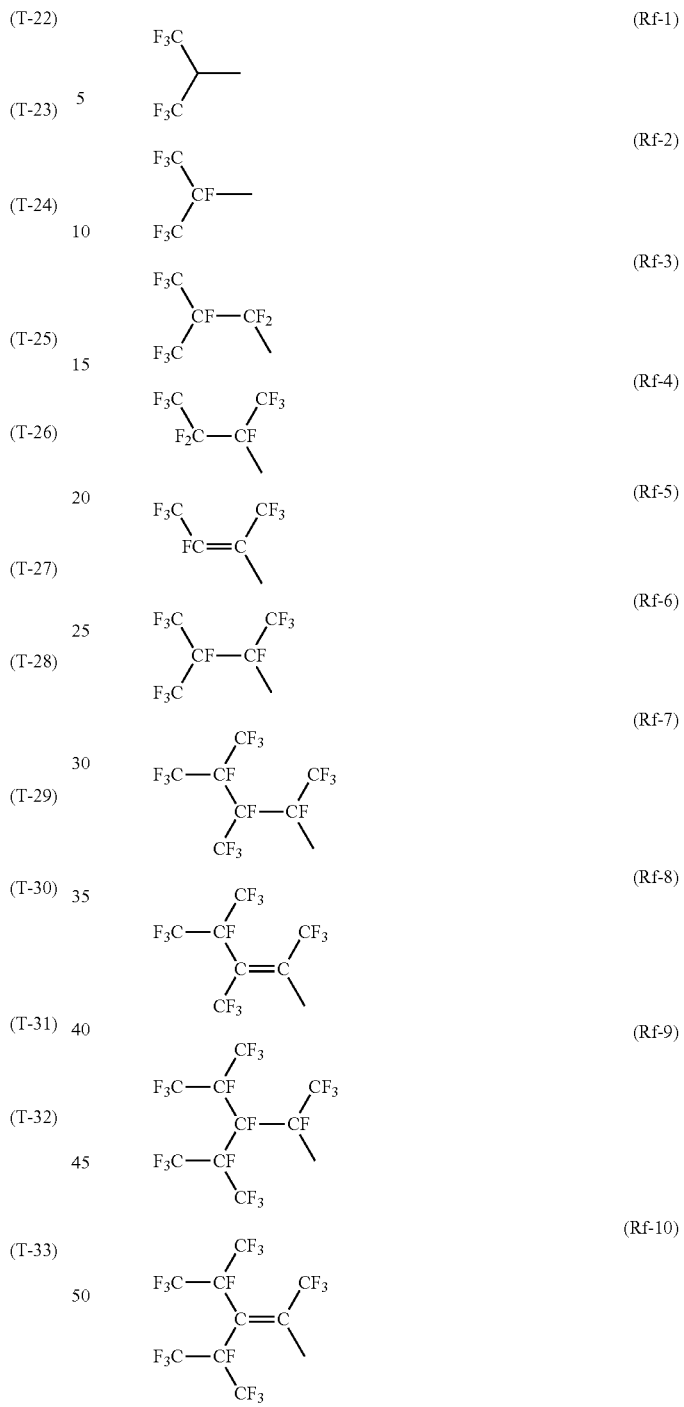

In Formula (I), l represents the number of "the divalent hydrocarbon groups having from 1 to 10 carbon atoms" represented by T, which is 0 or 1.

In Formula (I), Rf represents a branched hydrocarbon group having from 3 to 10 carbon atoms in which at least one hydrogen atom is substituted with a fluorine atom. Examples of the branched hydrocarbon group having from 3 to 10 carbon atoms in which at least one hydrogen atom is substituted with a fluorine atom represented by Rf (hereinafter, sometimes referred to as "the hydrocarbon group represented by Rf") include hydrocarbon groups having the following structures.

It is preferable that the hydrocarbon group represented by Rf be a hydrocarbon group having two or more branched chains, from the viewpoint of the dispersibility of fluororesin particles.

The number of the branched chains of the hydrocarbon group represented by Rf is the sum total of the number of side chains branched from the main chain and the number of side chains branched from the main chains in the respective side chains. In this case, the main chain in the hydrocarbon group represents a chain in which the highest number of carbon atoms constituting the hydrocarbon group are continuous; and the side chain represents a chain bonded to a main chain.

In the respective side chains, chains in which the highest number of carbon atoms constituting the side chains are continuous are regarded as main chains thereof; and chains bonded to the main chains are regarded as side chains thereof.

Regarding the number of branched chains of Rf-1 to Rf-10, the number of Rf-1, Rf-2, Rf-3, Rf-4, and Rf-5 is 1; the number of Rf-6 is 2; the number of Rf-7 and Rf-8 is 3; and the number of Rf-9 and Rf-10 is 4.

The number of branched chains in the hydrocarbon group represented by Rf is preferably greater than or equal to 2 and more preferably greater than or equal to 3.

When the hydrocarbon group represented by Rf includes plural branched chains, the number of carbon atoms is preferably from 5 to 10, more preferably from 7 to 10, and still more preferably 9 or 10, from the viewpoint of improving the dispersibility of fluororesin particles.

In addition, in the hydrocarbon group represented by Rf, from the viewpoint of the dispersibility of fluororesin particles, it is preferable that plural hydrogen atoms are substituted with fluorine atoms and it is more preferable that all the hydrogen atoms are substituted with fluorine atoms.

Furthermore, from the above-described viewpoints, in the hydrocarbon group represented by Rf, it is preferable that the number of carbon atoms be from 5 to 10 and all the hydrogen atoms be substituted with fluorine atoms; it is more preferable that the number of carbon atoms be from 7 to 10 and all the hydrogen atoms be substituted with fluorine atoms; and it is still more preferable that the number of carbon atoms be 9 or 10 and all the hydrogen atoms be substituted with fluorine atoms.

In Formula (I), m represents an integer of 1 to 4.

In Formula (I), when A represents an organic group derived from arylamine represented by Formula (II), represents preferably an integer of 1 to 3 and more preferably 1 or 2.

In Formula (I), when A represents an organic group derived from arylamine represented by Formula (III), m represents preferably an integer of 2 to 4, more preferably 2 or 3, and still more preferably 2.

Examples of the additive for an electrophotographic photoreceptor according to the exemplary embodiment include Compounds (I)-1 to (I)-16 shown in Tables 1 to 4.

TABLE 1

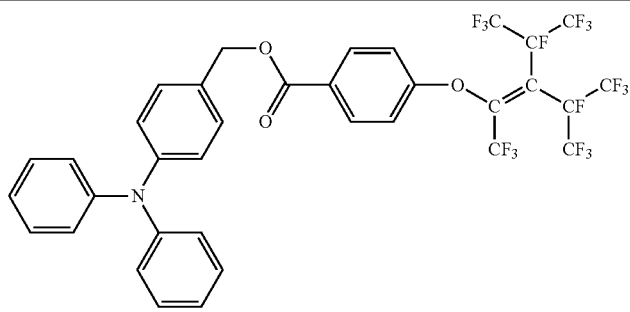

(I)-1

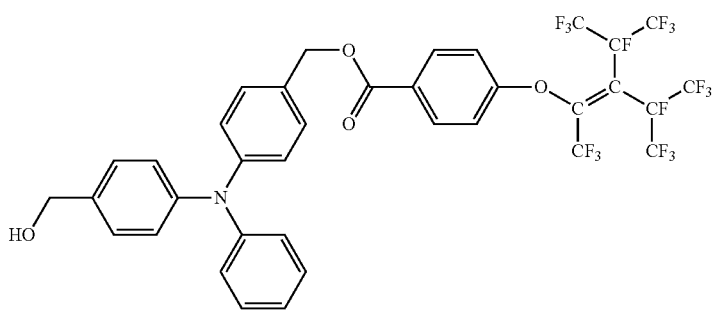

(I)-2

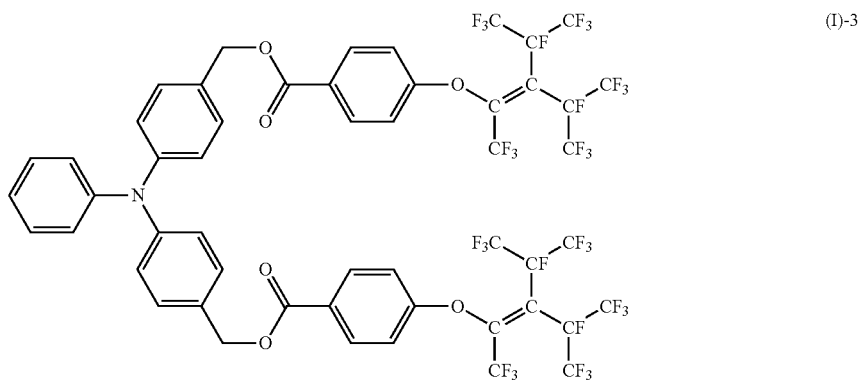

(I)-3

TABLE 1-continued
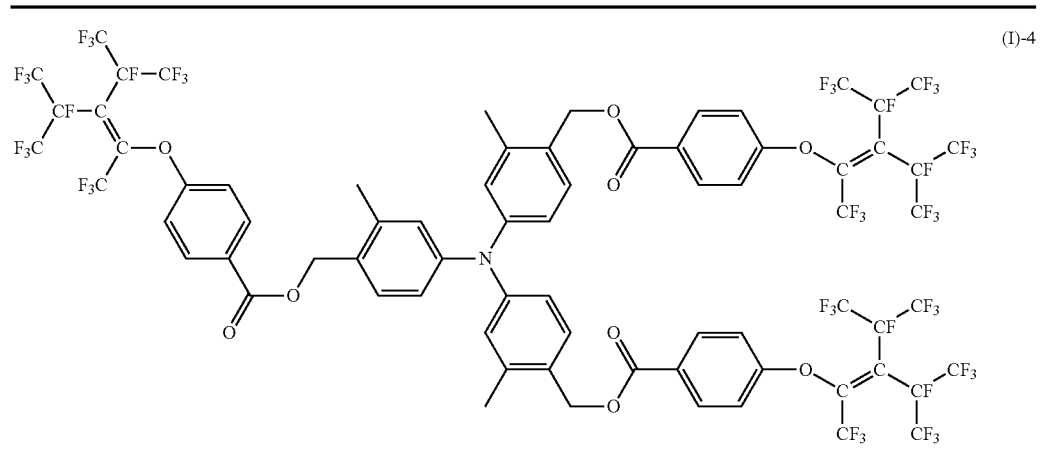
TABLE 2
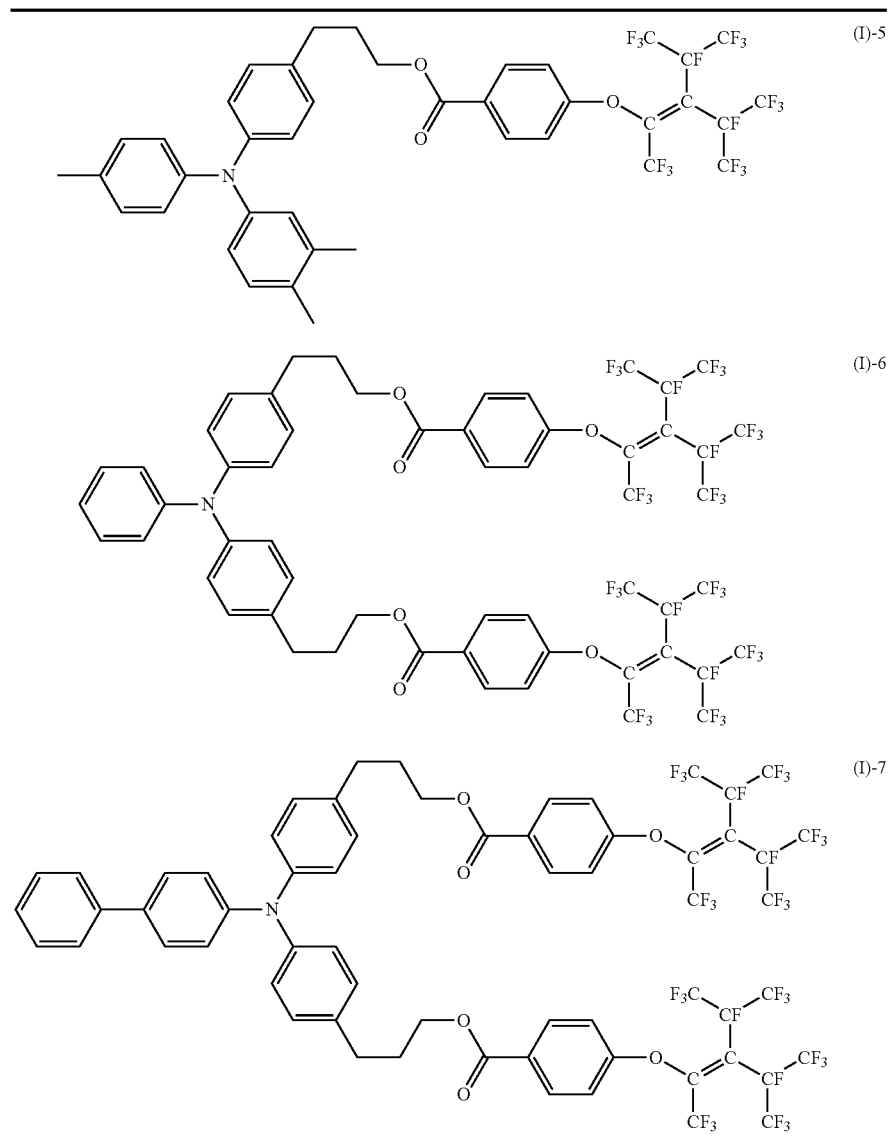

TABLE 2-continued
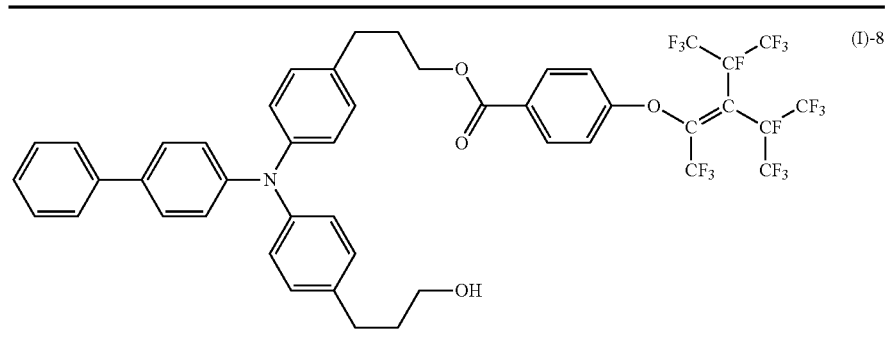
(I)-8
TABLE 3
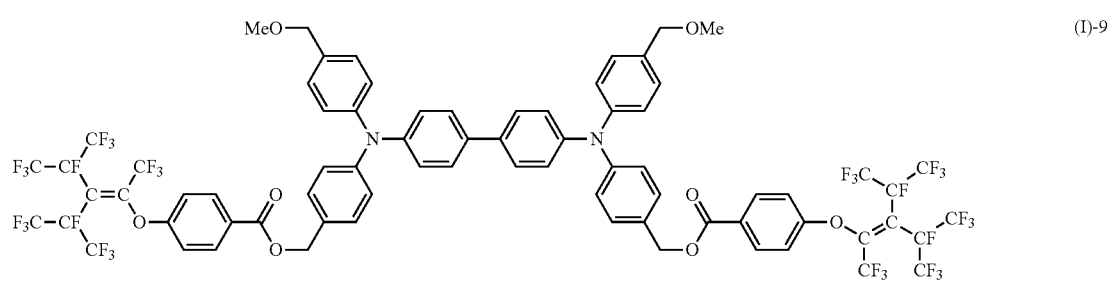
(I)-9
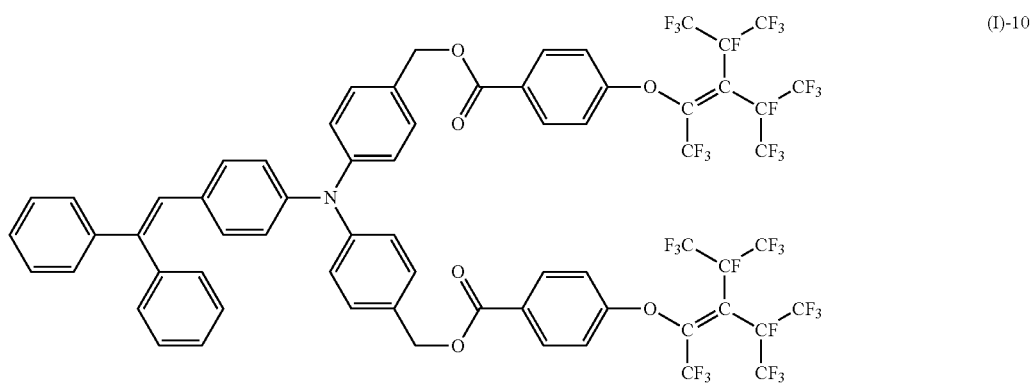
(I)-10
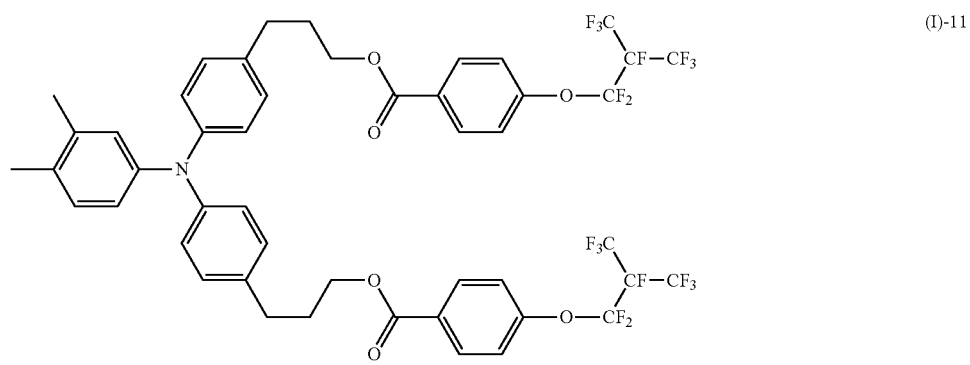
(I)-11

TABLE 3-continued
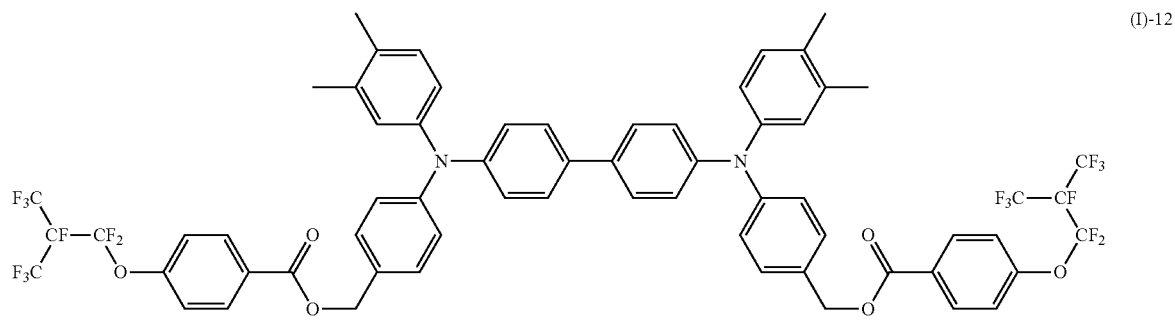
(I)-12
TABLE 4
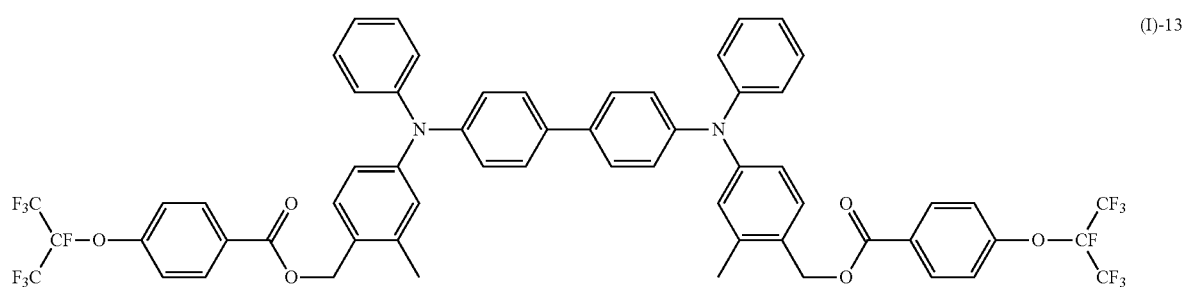
(I)-13
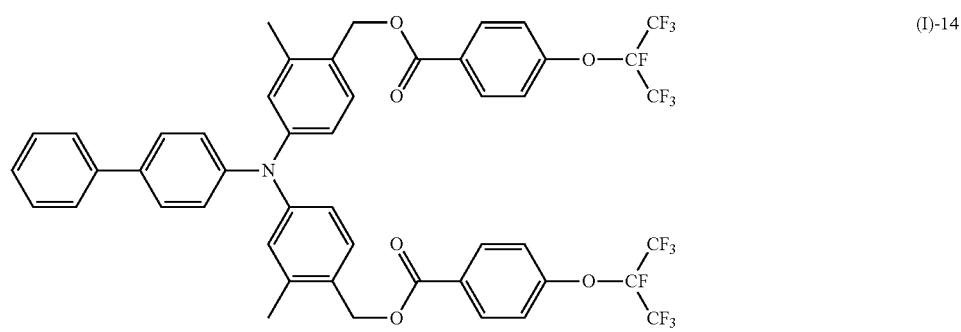
(I)-14
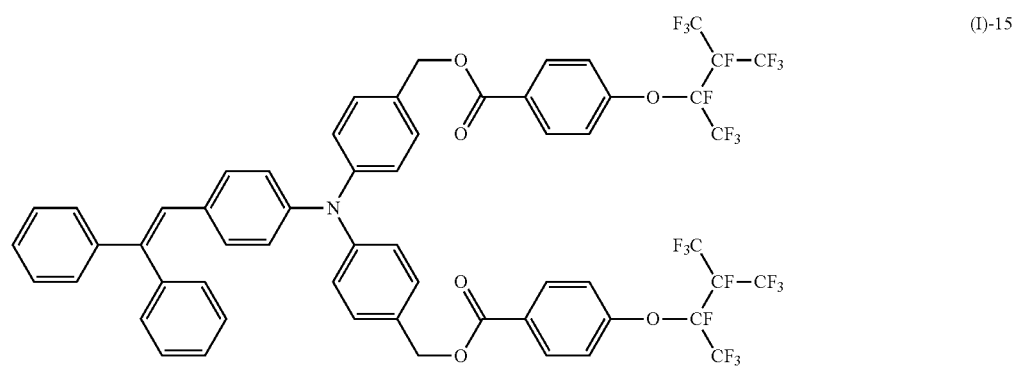
(I)-15

TABLE 4-continued

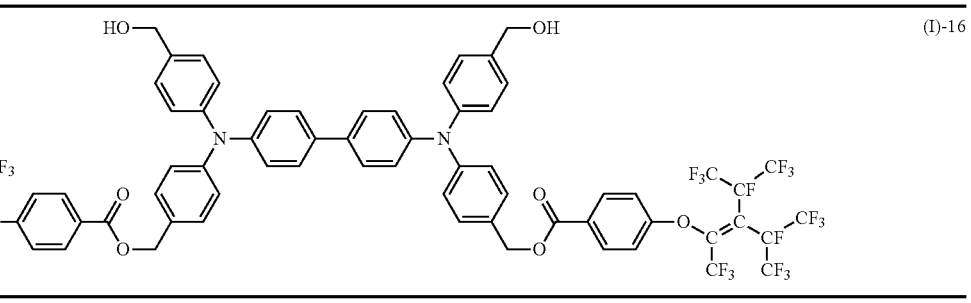
(I)-16

Furthermore, examples of the additive for an electrophotographic photoreceptor according to the exemplary embodiment include Compounds (I)-17 to (I)-115 shown in Tables 5 to 8.

In Tables 5 to 8, Ar-7 to Ar-24 represent substituents having the following structures; "*" represents a site bonded to a nitrogen atom; and "**" represents a site bonded to "-(T)$_1$-O—C(=O)—C$_6$H$_4$—O—Rf". T-1 and the like represent the divalent hydrocarbon groups which are described above as the specific examples of T in Formula (I); and Rf-1 and the like represent the hydrocarbon groups which are described above as the specific examples of RE in Formula (I).

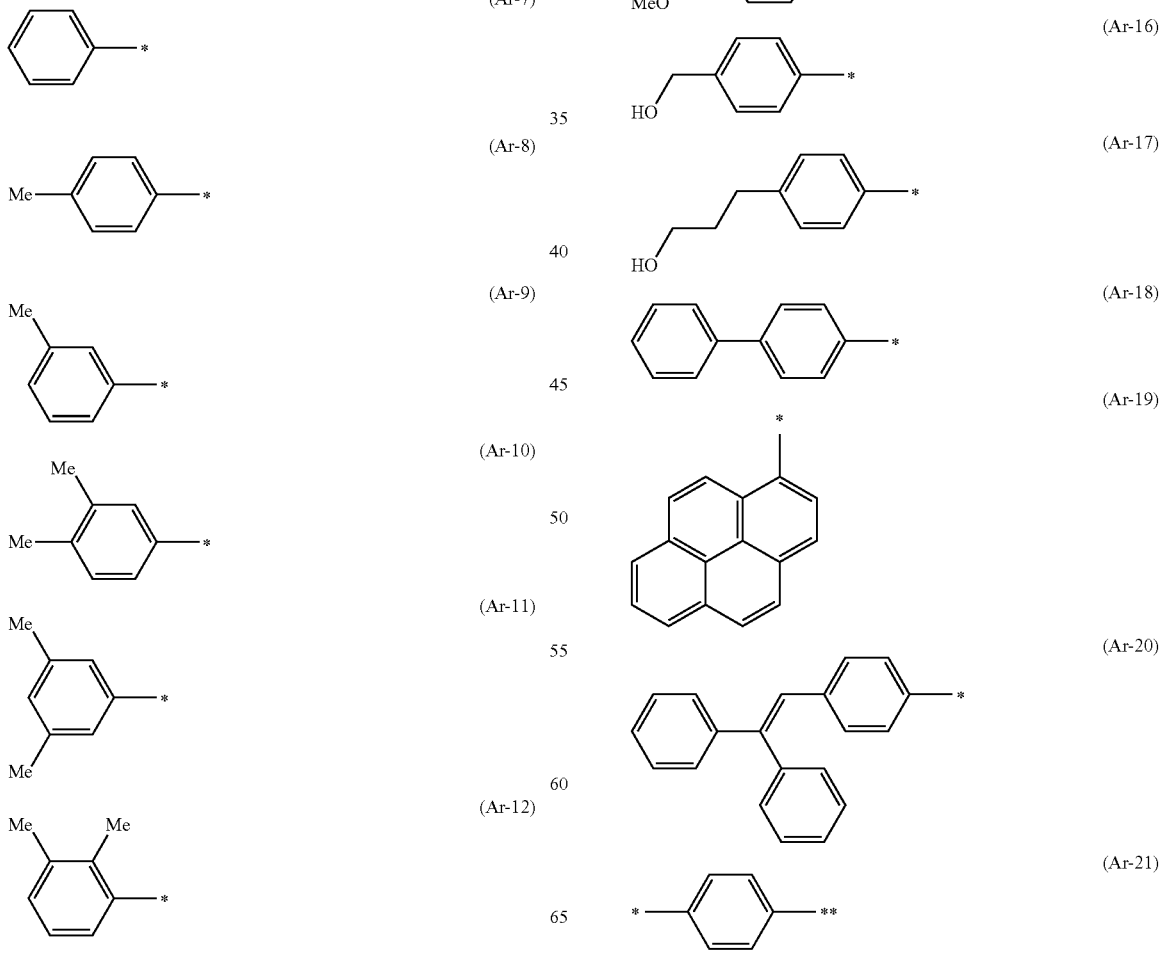

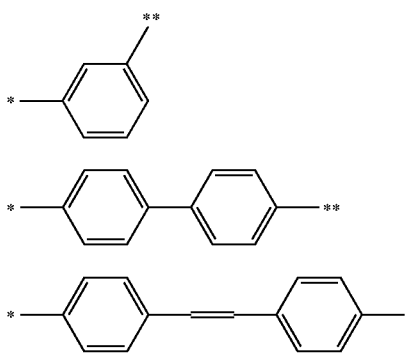

(Ar-22)

(Ar-23)

(Ar-24)

TABLE 5

| Compound | Ar¹ | Ar² | Ar³ | T | I | m | Rf |
|---|---|---|---|---|---|---|---|
| (I)-17 | Ar-7 | Ar-7 | Ar-21 | — | 0 | 1 | Rf-3 |
| (I)-18 | Ar-7 | Ar-7 | Ar-21 | T-1 | 1 | 1 | Rf-5 |
| (I)-19 | Ar-7 | Ar-7 | Ar-22 | T-4 | 1 | 1 | Rf-7 |
| (I)-20 | Ar-7 | Ar-7 | Ar-21 | T-18 | 1 | 1 | Rf-10 |
| (I)-21 | Ar-7 | Ar-7 | Ar-21 | T-32 | 1 | 1 | Rf-2 |
| (I)-22 | Ar-8 | Ar-8 | Ar-24 | T-1 | 1 | 1 | Rf-8 |
| (I)-23 | Ar-9 | Ar-9 | Ar-23 | T-5 | 1 | 1 | Rf-6 |
| (I)-24 | Ar-10 | Ar-10 | Ar-21 | T-1 | 1 | 1 | Rf-5 |
| (I)-25 | Ar-10 | Ar-10 | Ar-21 | T-4 | 1 | 1 | Rf-10 |
| (I)-26 | Ar-10 | Ar-8 | Ar-21 | T-3 | 1 | 1 | Rf-10 |
| (I)-27 | Ar-11 | Ar-11 | Ar-21 | T-4 | 1 | 1 | Rf-6 |
| (I)-28 | Ar-10 | Ar-18 | Ar-21 | T-4 | 1 | 1 | Rf-10 |
| (I)-29 | Ar-10 | Ar-19 | Ar-21 | T-25 | 1 | 1 | Rf-10 |
| (I)-30 | Ar-12 | Ar-7 | Ar-21 | T-3 | 1 | 1 | Rf-3 |
| (I)-31 | Ar-13 | Ar-7 | Ar-21 | T-3 | 1 | 1 | Rf-6 |
| (I)-32 | Ar-14 | Ar-7 | Ar-21 | T-4 | 1 | 1 | Rf-9 |
| (I)-33 | Ar-15 | Ar-7 | Ar-21 | T-4 | 1 | 1 | Rf-10 |
| (I)-34 | Ar-16 | Ar-7 | Ar-21 | T-4 | 1 | 1 | Rf-10 |
| (I)-35 | Ar-17 | Ar-7 | Ar-21 | T-4 | 1 | 1 | Rf-10 |
| (I)-36 | Ar-18 | Ar-7 | Ar-21 | T-4 | 1 | 1 | Rf-10 |
| (I)-37 | Ar-19 | Ar-7 | Ar-21 | T-4 | 1 | 1 | Rf-10 |
| (I)-38 | Ar-20 | Ar-7 | Ar-21 | T-4 | 1 | 1 | Rf-10 |
| (I)-39 | Ar-7 | Ar-21 | Ar-21 | T-3 | 1 | 2 | Rf-3 |
| (I)-40 | Ar-7 | Ar-22 | Ar-22 | T-20 | 1 | 2 | Rf-6 |
| (I)-41 | Ar-8 | Ar-21 | Ar-21 | T-3 | 1 | 2 | Rf-9 |
| (I)-42 | Ar-10 | Ar-21 | Ar-21 | T-4 | 1 | 2 | Rf-7 |
| (I)-43 | Ar-10 | Ar-23 | Ar-23 | T-4 | 1 | 2 | Rf-10 |
| (I)-44 | Ar-14 | Ar-21 | Ar-21 | T-4 | 1 | 2 | Rf-10 |
| (I)-45 | Ar-15 | Ar-21 | Ar-21 | T-4 | 1 | 2 | Rf-10 |
| (I)-46 | Ar-16 | Ar-21 | Ar-21 | T-4 | 1 | 2 | Rf-10 |
| (I)-47 | Ar-17 | Ar-21 | Ar-21 | T-4 | 1 | 2 | Rf-10 |
| (I)-48 | Ar-20 | Ar-21 | Ar-21 | T-4 | 1 | 2 | Rf-10 |
| (I)-49 | Ar-21 | Ar-21 | Ar-21 | T-1 | 1 | 3 | Rf-6 |
| (I)-50 | Ar-21 | Ar-21 | Ar-21 | T-4 | 1 | 3 | Rf-10 |

TABLE 6

| Compound | Ar⁴ | Ar⁵ | Ar⁶ | Ar⁷ | X | T | I | m | Rf |
|---|---|---|---|---|---|---|---|---|---|
| (I)-51 | Ar-7 | Ar-21 | Ar-7 | Ar-21 | IV | — | 0 | 2 | Rf-3 |
| (I)-52 | Ar-7 | Ar-21 | Ar-7 | Ar-21 | IV | T-1 | 1 | 2 | Rf-5 |
| (I)-53 | Ar-7 | Ar-21 | Ar-7 | Ar-21 | IV | T-5 | 1 | 2 | Rf-6 |
| (I)-54 | Ar-7 | Ar-21 | Ar-7 | Ar-21 | IV | T-4 | 1 | 2 | Rf-7 |
| (I)-55 | Ar-7 | Ar-22 | Ar-7 | Ar-22 | IV | T-4 | 1 | 2 | Rf-8 |
| (I)-56 | Ar-7 | Ar-22 | Ar-7 | Ar-22 | IV | T-5 | 1 | 2 | Rf-9 |
| (I)-57 | Ar-7 | Ar-23 | Ar-7 | Ar-23 | IV | T-1 | 1 | 2 | Rf-3 |
| (I)-58 | Ar-7 | Ar-23 | Ar-7 | Ar-23 | IV | T-4 | 1 | 2 | Rf-10 |
| (I)-59 | Ar-8 | Ar-22 | Ar-8 | Ar-22 | IV | T-4 | 1 | 2 | Rf-7 |
| (I)-60 | Ar-10 | Ar-22 | Ar-10 | Ar-22 | IV | T-8 | 1 | 2 | Rf-3 |
| (I)-61 | Ar-10 | Ar-22 | Ar-10 | Ar-22 | IV | T-25 | 1 | 2 | Rf-6 |
| (I)-62 | Ar-12 | Ar-21 | Ar-12 | Ar-21 | IV | T-1 | 1 | 2 | Rf-7 |
| (I)-63 | Ar-12 | Ar-21 | Ar-12 | Ar-21 | IV | T-4 | 1 | 2 | Rf-10 |
| (I)-64 | Ar-13 | Ar-21 | Ar-13 | Ar-21 | IV | T-4 | 1 | 2 | Rf-10 |
| (I)-65 | Ar-14 | Ar-21 | Ar-14 | Ar-21 | IV | T-4 | 1 | 2 | Rf-10 |

TABLE 6-continued

| Compound | Ar⁴ | Ar⁵ | Ar⁶ | Ar⁷ | X | T | I | m | Rf |
|---|---|---|---|---|---|---|---|---|---|
| (I)-66 | Ar-15 | Ar-21 | Ar-15 | Ar-21 | IV | T-4 | 1 | 2 | Rf-10 |
| (I)-67 | Ar-16 | Ar-21 | Ar-16 | Ar-21 | IV | T-4 | 1 | 2 | Rf-10 |
| (I)-68 | Ar-17 | Ar-21 | Ar-17 | Ar-21 | IV | T-4 | 1 | 2 | Rf-10 |
| (I)-69 | Ar-18 | Ar-21 | Ar-18 | Ar-21 | IV | T-4 | 1 | 2 | Rf-10 |
| (I)-70 | Ar-20 | Ar-21 | Ar-20 | Ar-21 | IV | T-4 | 1 | 2 | Rf-10 |
| (I)-71 | Ar-21 | Ar-21 | Ar-21 | Ar-21 | IV | — | 0 | 4 | Rf-3 |
| (I)-72 | Ar-21 | Ar-21 | Ar-21 | Ar-21 | IV | T-4 | 1 | 4 | Rf-6 |
| (I)-73 | Ar-21 | Ar-21 | Ar-21 | Ar-21 | IV | T-26 | 1 | 4 | Rf-10 |

TABLE 7

| Compound | Ar⁴ | Ar⁵ | Ar⁶ | Ar⁷ | X | T | I | m | Rf |
|---|---|---|---|---|---|---|---|---|---|
| (I)-74 | Ar-7 | Ar-21 | Ar-7 | Ar-21 | V | T-1 | 1 | 2 | Rf-1 |
| (I)-75 | Ar-7 | Ar-21 | Ar-7 | Ar-21 | V | T-3 | 1 | 2 | Rf-6 |
| (I)-76 | Ar-7 | Ar-21 | Ar-7 | Ar-21 | V | T-4 | 1 | 2 | Rf-7 |
| (I)-77 | Ar-7 | Ar-21 | Ar-7 | Ar-21 | V | T-26 | 1 | 2 | Rf-8 |
| (I)-78 | Ar-7 | Ar-23 | Ar-7 | Ar-23 | V | T-1 | 1 | 2 | Rf-9 |
| (I)-79 | Ar-7 | Ar-23 | Ar-7 | Ar-23 | V | T-4 | 1 | 2 | Rf-10 |
| (I)-80 | Ar-8 | Ar-22 | Ar-8 | Ar-22 | V | T-4 | 1 | 2 | Rf-10 |
| (I)-81 | Ar-10 | Ar-21 | Ar-10 | Ar-21 | V | T-1 | 1 | 2 | Rf-1 |
| (I)-82 | Ar-10 | Ar-21 | Ar-10 | Ar-21 | V | T-4 | 1 | 2 | Rf-6 |
| (I)-83 | Ar-10 | Ar-21 | Ar-10 | Ar-21 | V | T-4 | 1 | 2 | Rf-9 |
| (I)-84 | Ar-10 | Ar-21 | Ar-10 | Ar-21 | V | T-28 | 1 | 2 | Rf-10 |
| (I)-85 | Ar-10 | Ar-23 | Ar-10 | Ar-23 | V | T-4 | 1 | 2 | Rf-3 |
| (I)-86 | Ar-12 | Ar-21 | Ar-12 | Ar-21 | V | T-1 | 1 | 2 | Rf-10 |
| (I)-87 | Ar-13 | Ar-21 | Ar-13 | Ar-21 | V | T-4 | 1 | 2 | Rf-10 |
| (I)-88 | Ar-14 | Ar-21 | Ar-14 | Ar-21 | V | T-4 | 1 | 2 | Rf-10 |
| (I)-89 | Ar-15 | Ar-21 | Ar-15 | Ar-21 | V | T-4 | 1 | 2 | Rf-10 |
| (I)-90 | Ar-16 | Ar-21 | Ar-16 | Ar-21 | V | T-4 | 1 | 2 | Rf-10 |
| (I)-91 | Ar-17 | Ar-21 | Ar-17 | Ar-21 | V | T-4 | 1 | 2 | Rf-10 |
| (I)-92 | Ar-18 | Ar-22 | Ar-18 | Ar-22 | V | T-4 | 1 | 2 | Rf-10 |
| (I)-93 | Ar-20 | Ar-21 | Ar-20 | Ar-21 | V | T-4 | 1 | 2 | Rf-10 |
| (I)-94 | Ar-21 | Ar-21 | Ar-21 | Ar-21 | V | T-1 | 1 | 4 | Rf-3 |
| (I)-95 | Ar-21 | Ar-21 | Ar-21 | Ar-21 | V | T-4 | 1 | 4 | Rf-10 |

TABLE 8

| Compound | Ar⁴ | Ar⁵ | Ar⁶ | Ar⁷ | X | T | I | m | Rf |
|---|---|---|---|---|---|---|---|---|---|
| (I)-96 | Ar-7 | Ar-21 | Ar-7 | Ar-21 | VI | T-1 | 1 | 2 | Rf-3 |
| (I) 97 | Ar-7 | Ar-21 | Ar-7 | Ar-21 | VI | T-4 | 1 | 2 | Rf-6 |
| (I)-98 | Ar-7 | Ar-21 | Ar-7 | Ar-21 | VI | T-4 | 1 | 2 | Rf-7 |
| (I)-99 | Ar-7 | Ar-21 | Ar-7 | Ar-21 | VI | T-33 | 1 | 2 | Rf-8 |
| (I)-100 | Ar-7 | Ar-23 | Ar-7 | Ar-23 | VI | T-1 | 1 | 2 | Rf-9 |
| (I)-101 | Ar-7 | Ar-23 | Ar-7 | Ar-23 | VI | T-20 | 1 | 2 | Rf-10 |
| (I)-102 | Ar-10 | Ar-21 | Ar-10 | Ar-21 | VI | T-1 | 1 | 2 | Rf-3 |
| (I)-103 | Ar-10 | Ar-21 | Ar-10 | Ar-21 | VI | T-4 | 1 | 2 | Rf-6 |
| (I)-104 | Ar-10 | Ar-21 | Ar-10 | Ar-21 | VI | T-4 | 1 | 2 | Rf-10 |
| (I)-105 | Ar-12 | Ar-21 | Ar-12 | Ar-21 | VI | T-4 | 1 | 2 | Rf-3 |
| (I)-106 | Ar-12 | Ar-21 | Ar-12 | Ar-21 | VI | T-4 | 1 | 2 | Rf-6 |
| (I)-107 | Ar-13 | Ar-21 | Ar-13 | Ar-21 | VI | T-4 | 1 | 2 | Rf-9 |
| (I)-108 | Ar-14 | Ar-21 | Ar-14 | Ar-21 | VI | T-4 | 1 | 2 | Rf-10 |
| (I)-109 | Ar-15 | Ar-21 | Ar-15 | Ar-21 | VI | T-4 | 1 | 2 | Rf-10 |
| (I)-110 | Ar-16 | Ar-21 | Ar-16 | Ar-21 | VI | T-4 | 1 | 2 | Rf-10 |
| (I)-111 | Ar-17 | Ar-21 | Ar-17 | Ar-21 | VI | T-4 | 1 | 2 | Rf-10 |
| (I)-112 | Ar-18 | Ar-21 | Ar-18 | Ar-21 | VI | T-4 | 1 | 2 | Rf-10 |
| (I)-113 | Ar-20 | Ar-21 | Ar-20 | Ar-21 | VI | T-4 | 1 | 2 | Rf-10 |
| (I)-114 | Ar-21 | Ar-21 | Ar-21 | Ar-21 | VI | T-1 | 1 | 2 | Rf-10 |
| (I)-115 | Ar-21 | Ar-21 | Ar-21 | Ar-21 | VI | T-4 | 1 | 4 | Rf-10 |

The additive for an electrophotographic photoreceptor according to the exemplary embodiment is synthesized by esterification using an ester exchange reaction of, for example, an arylamine compound having a hydroxyl group with a fluorine-containing ester compound. In addition, for example, as disclosed in JP-B-59-37000, the synthesis may be performed by causing a fluorine-containing carboxylic acid compound to react with a halogenating agent to obtain an acid halide and conducting a dehydrohalogenation reaction with an arylamine compound having a hydroxyl group.

For example, as described in the fourth series of Experimental Chemistry, vol. 28, p. 217, the ester exchange reaction is conducted by mixing an arylamine compound having a hydroxyl group, a fluorine-containing ester compound, and an organometallic compound such as titanium, tin, or zinc and heating the mixture.

The amount of the fluorine-containing ester compound used is preferably 1 equivalent or more, more preferably 1.2 equivalents or more, and still more preferably 1.5 equivalents or more, with respect to the hydroxyl group of the arylamine compound having a hydroxyl group.

In the ester exchange reaction, an inorganic acid such as sulfuric acid or phosphoric acid; titanium alkoxide; an acetate or a carbonate of calcium, cobalt, or the like; an oxide of zinc, lead, or the like; or the like may be further added as a catalyst. The amount of the catalyst used is preferably from 1/10,000 part by weight to 1 part by weight and more preferably from 1/1,000 part by weight to 1/2 part by weight, with respect to 1 part by weight of the arylamine compound having a hydroxyl group.

The ester exchange reaction is conducted at a reaction temperature of preferably 100° C. to 300° C. and more preferably higher than or equal to the boiling temperature of alcohol which is to be desorbed. It is preferable that the ester exchange reaction be conducted in inert gas such as nitrogen or argon. In the ester exchange reaction, a high-boiling point solvent such as p-cymene or 1-chloronaphthalene may be used.

Examples of a method of synthesizing the arylamine compound having a hydroxyl group include a method of formylating an arylamine compound using N,N-dimethylformamide, phosphorus oxychloride, and the like and conducting reduction with sodium borohydride; and a method of reducing an ester group of an arylamine compound having an ester group to alcohol with a reducing agent such as lithium aluminum hydride.

The fluorine-containing ester compound is synthesized by dehydration of, for example, a fluorine-containing carboxylic acid and alcohol using an acid catalyst.

Electrophotographic Photoreceptor

An electrophotographic photoreceptor according to the exemplary embodiment includes a conductive substrate and a photosensitive layer that is provided on the conductive substrate, in which an outermost surface layer of the electrophotographic photoreceptor is a layer formed of a composition which includes a charge transport material, fluororesin particles, and the additive for an electrophotographic photoreceptor according to the exemplary embodiment.

In this case, the composition may include one or two or more kinds of the additives for an electrophotographic photoreceptor according to the exemplary embodiment.

In addition, "an outermost surface layer which is a layer formed of a composition which includes a charge transport material, fluororesin particles, and the additive for an electrophotographic photoreceptor according to the exemplary embodiment" includes layers described in the following (1) and (2).
(1) The outermost surface layer which is a layer formed of a composition which includes a binder resin, a charge transport material, fluororesin particles, and the additive for an electrophotographic photoreceptor according to the exemplary embodiment
(2) The outermost surface layer which is a curable layer formed of a composition which includes a reactive charge transport material, fluororesin particles, and the additive for an electrophotographic photoreceptor according to the exemplary embodiment According to the exemplary embodiment, there is provided an electrophotographic photoreceptor which further suppresses the change in electrical characteristics, as compared to a case in which the outermost layer is a layer formed of a composition which includes a charge transport material, fluororesin particles, a compound having a charge transport structure and a fluorinated hydrocarbon group other than the compounds represented by Formula (I).

An electrophotographic photoreceptor according to another embodiment includes a conductive substrate and a photosensitive layer that is provided on the conductive substrate, in which the outermost surface layer is a layer formed of a composition which includes a charge transport material and the additive for an electrophotographic photoreceptor according to the exemplary embodiment. That is, in the electrophotographic photoreceptor according to this exemplary embodiment, the outermost surface layer does not include fluororesin particles.

In this case, the composition may include one or two or more kinds of the additives for an electrophotographic photoreceptor according to the exemplary embodiment.

In addition, "the outermost surface layer which is a layer formed of a composition which includes a charge transport material and the additive for an electrophotographic photoreceptor according to the exemplary embodiment" includes layers described in the following (3) and (4).
(3) The outermost surface layer which is a layer formed of a composition which includes a binder resin, a charge transport material and the additive for an electrophotographic photoreceptor according to the exemplary embodiment
(4) The outermost surface layer which is a curable layer formed of a composition which includes a reactive charge transport material and the additive for an electrophotographic photoreceptor according to the exemplary embodiment According to this exemplary embodiment, there is provided an electrophotographic photoreceptor with a superior cleaning property, as compared to a case in which the outermost layer is a layer formed of a composition which includes a charge transport material and a compound having a charge transport structure and a fluorinated hydrocarbon group other than the compounds represented by Formula (I).

Hereinafter, the electrophotographic photoreceptor according to this exemplary embodiment will be described in detail with reference to the drawings.

Figure 2:
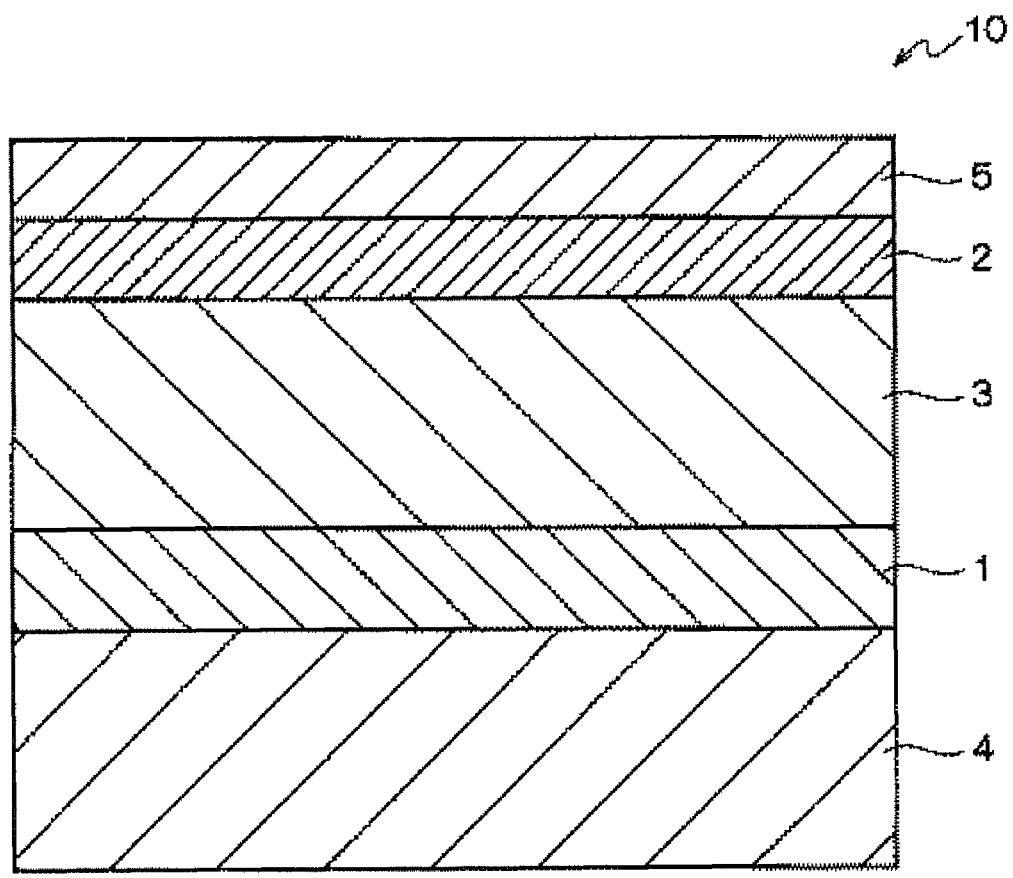
FIG. 2 is a cross-sectional view schematically illustrating a part of an electrophotographic photoreceptor according to another exemplary embodiment of the invention.
Figure 3:
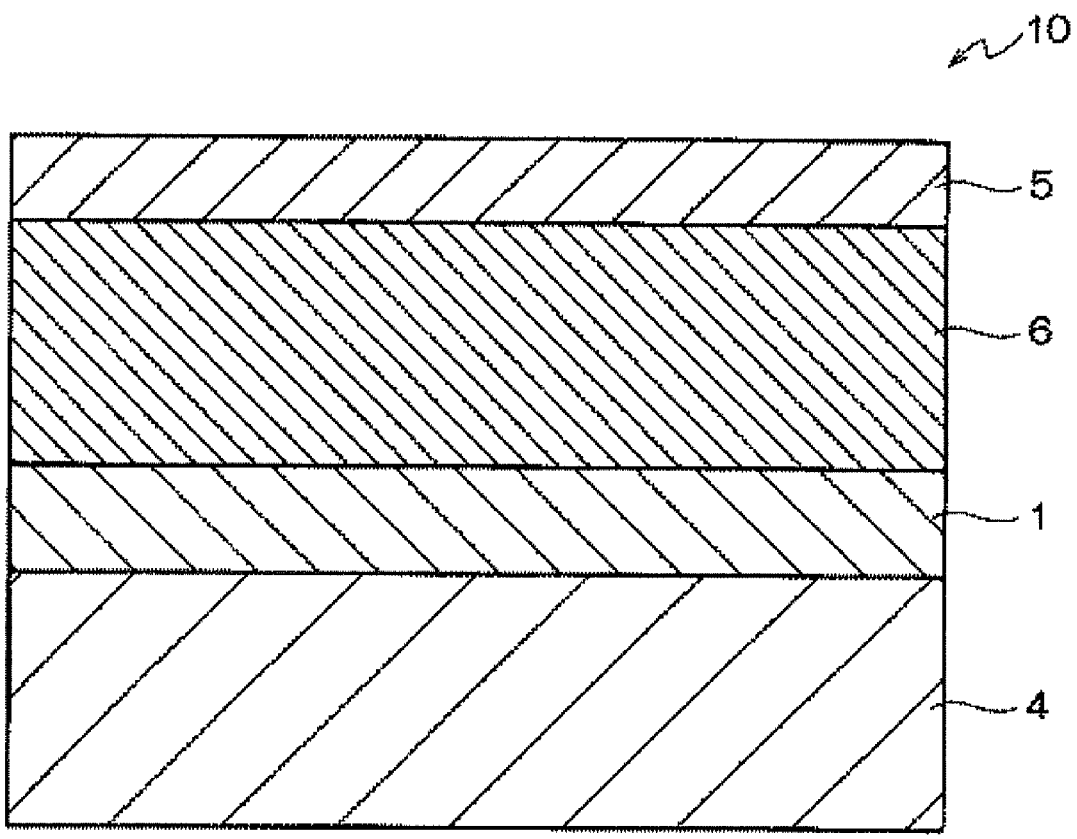
FIG. 3 is a cross-sectional view schematically illustrating a part of an electrophotographic photoreceptor according to another exemplary embodiment of the invention.

FIGS. 1 to 3 each schematically show the cross-section of a part of an electrophotographic photoreceptor 10 according to this exemplary embodiment.

In the electrophotographic photoreceptor 10 shown in FIG. 1, an undercoat layer 1 is provided on a conductive support 4, a charge generation layer 2 and a charge transport layer 3 as photosensitive layers are provided on the undercoat layer, and a surface protective layer 5 as an outermost surface layer is provided thereon.

In the electrophotographic photoreceptor 10 shown in FIG. 2, although photosensitive layers having separate functions are provided such as a charge generation layer 2 and a charge transport layer 3 as in the electrophotographic photoreceptor 10 shown in FIG. 1, the charge transport layer 3, the charge generation layer 2, and a surface protective layer 5 are provided in that order on an undercoat layer 1.

In the electrophotographic photoreceptor 10 shown in FIG. 3, a charge generation material and a charge transport material are contained in the same layer, that is, a single layer-type photosensitive layer 6 (charge generation/charge transport layer), and a surface protective layer 5 is provided on the photosensitive layer 6.

In the electrophotographic photoreceptors 10 shown in FIGS. 1 to 3, the surface protective layer 5 is provided on the photosensitive layer, and the surface protective layer 5 serves as an outermost surface layer. However, when the surface protective layer 5 is not provided, the uppermost layer of the photosensitive layer serves as an outermost surface layer. Specifically, in the case of a layer configuration that is the same as the layer configuration of the electrophotographic photoreceptor 10 shown in FIG. 1 except that the surface protective layer 5 is not provided, the charge transport layer 3 corresponds to an outermost surface layer. In addition, in the case of a layer configuration that is the same as the layer configuration of the electrophotographic photoreceptor 10 shown in FIG. 3 except that the surface protective layer 5 is not provided, the single layer-type photosensitive layer 6 corresponds to an outermost surface layer.

Hereinafter, the respective elements will be described on the basis of the electrophotographic photoreceptors 10 shown in the drawings as representative examples. The reference numbers will be omitted.

Conductive Substrate

As the conductive substrate, any one may be used if it has been used hitherto. Examples thereof include paper and plastic films coated or impregnated with a conductivity imparting agent, such as plastic films having a thin film (for example, metals such as aluminum, nickel, chromium, and stainless steel, and films of aluminum, titanium, nickel, chromium, stainless steel, gold, vanadium, tin oxide, indium oxide, and indium tin oxide (ITO)) provided thereon. The shape of the substrate is not limited to a cylindrical shape, and may be a sheet shape or a plate shape.

When a metallic pipe is used as the conductive substrate, the surface thereof may be used as it is, or may be subjected to specular machining, etching, anodization, coarse machining, centerless grinding, sand blasting, wet honing, or the like in advance.

Undercoat Layer

The undercoat layer is provided as necessary to prevent light reflection on the surface of the conductive substrate, and to prevent unnecessary carriers from flowing from the conductive substrate to the photosensitive layer.

The undercoat layer includes, for example, a binder resin, and if necessary, other additives.

Examples of the binder resin included in the undercoat layer include known polymeric resin compounds e.g., acetal resins such as polyvinyl butyral, polyvinyl alcohol resins, casein, polyamide resins, cellulose resins, gelatin, polyurethane resins, polyester resins, methacrylic resins, acrylic resins, polyvinyl chloride resins, polyvinyl acetate resins, vinyl chloride-vinyl acetate-maleic anhydride resins, silicone resins, silicone-alkyd resins, phenol resins, phenol-formaldehyde resins, melamine resins, and urethane resins; charge-transporting resins having a charge transport group; and conductive resins such as polyaniline. Among them, resins insoluble in the coating solvent of the upper layer are preferably used, and phenol resins, phenol-formaldehyde resins, melamine resins, urethane resins, and epoxy resins, and the like are particularly preferably used.

The undercoat layer may contain a metallic compound such as a silicon compound, an organic zirconium compound, an organic titanium compound, and an organic aluminum compound.

The ratio of the metallic compound to the binder resin is not particularly limited, and may be set so that desired electrophotographic photoreceptor characteristics are obtained.

Resin particles may be added to the undercoat layer in order to adjust surface roughness. Examples of the resin particles include silicone resin particles and cross-linked polymethylmethacrylate (PMMA) resin particles. After forming the undercoat layer, the surface thereof may be polished in order to adjust surface roughness. Examples of the polishing method include buff polishing, sand blasting, wet honing, and grinding.

Here, examples of the configuration of the undercoat layer include a configuration in which at least a binder resin and conductive particles are contained. The conductive particles may have a conductive property in which the volume resistivity is, for example, less than $10^7$ Ω·cm.

Examples of the conductive particles include metallic particles (aluminum particles, copper particles, nickel particles, silver particles, and the like), conductive metallic oxide particles (antimony oxide particles, indium oxide particles, tin oxide particles, zinc oxide particles, and the like), and conductive substance particles (carbon fiber particles, carbon black particles, and graphite powder particles). Among them, conductive metallic oxide particles are preferable. The conductive particles may be used in mixture of two or more types.

In addition, the conductive particles may be used after being surface-treated with a hydrophobizing agent or the like (for example, coupling agent) for adjusting the resistance.

The content of the conductive particles is preferably 10% by weight to 80% by weight, and more preferably 40% by weight to 80% by weight with respect to the binder resin.

In the formation of the undercoat layer, a coating liquid for undercoat layer formation is used in which the above components are added to a solvent.

In addition, as a method of dispersing the particles in the coating liquid for undercoat layer formation, a media disperser such as a ball mill, a vibrating ball mill, an attritor, a sand mill, or a horizontal sand mill, or a media-less disperser such as a stirrer, an ultrasonic disperser, a roll mill, or a high-pressure homogenizer is used. Here, examples of the high-pressure homogenizer include a collision-type homogenizer in which a dispersion is dispersed under high pressure by liquid-liquid collision or liquid-wall collision, and a penetration-type homogenizer in which a dispersion is dispersed by allowing it to penetrate through a minute channel under high pressure.

Examples of the method of coating the conductive substrate with the coating liquid for undercoat layer formation include a dipping coating method, an extrusion coating method, a wire bar coating method, a spray coating method, a blade coating method, a knife coating method, and a curtain coating method.

The thickness of the undercoat layer is preferably 15 μm or greater, and more preferably from 20 μm to 50 μm.

Here, although omitted in the drawings, an intermediate layer may be further provided between the undercoat layer and the photosensitive layer. Examples of the binder resin for use in the intermediate layer include polymeric resin compounds e.g., acetals resin such as polyvinyl butyral, polyvinyl alcohol resins, casein, polyamide resins, cellulose resins, gelatin, polyurethane resins, polyester resins, methacrylic resins, acrylic resins, polyvinyl chloride resins, polyvinyl acetate resins, vinyl chloride-vinyl acetate-maleic anhydride resins, silicone resins, silicone-alkyd resins, phenol-formaldehyde resins, and melamine resins; and organic metallic compounds containing zirconium, titanium, aluminum, manganese, and silicon atoms. These compounds may be used singly or as a mixture or polycondensate of the plural compounds. Among them, an organic metallic compound containing zirconium or silicon is preferable because it has a low residual potential, and thus a change in potential due to the environment is small, and a change in potential due to the repeated use is small.

In the formation of the intermediate layer, a coating liquid for intermediate layer formation is used in which the above components are added to a solvent.

As a coating method for forming the intermediate layer, a general method is used such as a dipping coating method, an extrusion coating method, a wire bar coating method, a spray coating method, a blade coating method, a knife coating method, or a curtain coating method.

The intermediate layer improves the coating property of the upper layer and also functions as an electric blocking layer. However, when the thickness is excessively large, an electric barrier becomes excessively strong, which may cause desensitization or an increase in potential due to the repeated use. Accordingly, when an intermediate layer is formed, the thickness may be set to from 0.1 μm to 3 μm. In this case, the intermediate layer may be used as the undercoat layer.

Charge Generation Layer

The charge generation layer includes, for example, a charge generation material and a binder resin. Examples of the charge generation material include phthalocyanine pigments such as metal-free phthalocyanine, chlorogallium phthalocyanine, hydroxygallium phthalocyanine, dichlorotin phthalocyanine, and titanyl phthalocyanine. Particularly, there are exemplified a chlorogallium phthalocyanine crystal having strong diffraction peaks at least at Bragg angles (2θ±0.2°) of 7.4°, 16.6°, 25.5°, and 28.3° with respect to CuKα characteristic X-ray, a metal-free phthalocyanine crystal having strong diffraction peaks at least at Bragg angles (2θ±0.2°) of 7.7°, 9.3°, 16.9°, 17.5°, 22.4°, and 28.8° with respect to CuKα characteristic X-ray, a hydroxygallium phthalocyanine crystal having strong diffraction peaks at least at Bragg angles (2θ±0.2°) of 7.5°, 9.9°, 12.5°, 16.3°, 18.6°, 25.1°, and 28.3° with respect to CuKα characteristic X-ray, and a titanyl phthalocyanine crystal having strong diffraction peaks at least at Bragg angles (2θ±0.2°) of 9.6°, 24.1°, and 27.2° with respect to CuKα characteristic X-ray. Other examples of the charge generation material include quinone pigments, perylene pigments, indigo pigments, bisbenzimidazole pigments, anthrone pigments, and quinacridone pigments. These charge generation materials may be used singly or in mixture of two or more types.

Examples of the binder resins constituting the charge generation layer include polycarbonate resins such as a polybisphenol-A carbonate and a polybisphenol-Z carbonate, acrylic resins, methacrylic resins, polyarylate resins, polyester resins, polyvinyl chloride resins, polystyrene resins, acrylonitrile-styrene copolymer resins, acrylonitrile-butadiene copolymer resins, polyvinyl acetate resins, polyvinyl formal resins, polysulfone resins, styrene-butadiene copolymer resins, vinylidene chloride-acrylonitrile copolymer resins, vinyl chloride-vinyl acetate-maleic anhydride resins, silicone resins, phenol-formaldehyde resins, polyacrylamide resins, polyamide resins, and poly-N-vinylcarbazole resins. These binder resins may be used singly or in mixture of two or more types.

The blending ratio of the charge generation material to the binder resin is, for example, preferably from 10:1 to 1:10.

In the formation of the charge generation layer, a coating liquid for charge generation layer formation is used in which the above components are added to a solvent.

As a method of dispersing the particles (for example, charge generation material) in the coating liquid for charge generation layer formation, a media disperser such as a ball mill, a vibrating ball mill, an attritor, a sand mill, or a horizontal sand mill, or a media-less disperser such as a stirrer, an ultrasonic disperser, a roll mill, or a high-pressure homogenizer is used. Examples of the high-pressure homogenizer include a collision-type homogenizer in which a dispersion is dispersed under high pressure by liquid-liquid collision or liquid-wall collision, and a penetration-type homogenizer in which a dispersion is dispersed by allowing it to penetrate through a minute channel under high pressure.

Examples of the method of coating the undercoat layer with the coating liquid for charge generation layer formation include a dipping coating method, an extrusion coating method, a wire bar coating method, a spray coating method, a blade coating method, a knife coating method, and a curtain coating method.

The thickness of the charge generation layer is preferably set to from 0.01 μm to 5 μm, and more preferably from 0.05 μm to 2.0 μm.

Charge Transport Layer

A charge transport layer includes a charge transport material and optionally may further include a binder resin. When the charge transport layer corresponds to the outermost surface layer, the charge transport layer includes the additive for an electrophotographic photoreceptor according to the exemplary embodiment.

Examples of the charge transport material include hole transport materials such as oxadiazole derivatives (for example, 2,5-bis(p-diethylaminophenyl)-1,3,4-oxadiazole), pyrazoline derivatives (for example, 1,3,5-triphenyl-pyrazoline and 1-[pyridyl-(2)]-3-(p-diethylaminostyryl)-5-(p-diethylamino styryl)pyrazoline), aromatic tertiary amino compounds (for example, triphenylamine, N,N'-bis(3,4-dimethylphenyl)biphenyl-4-amine, tri(p-methylphenyl)aminyl-4-amine, and dibenzyl aniline), aromatic tertiary diamino compounds (for example, N,N'-bis(3-methylphenyl)-N,N'-diphenyl benzidine), 1,2,4-triazine derivatives (for example, 3-(4'-dimethylaminophenyl)-5,6-di-(4'-methoxyphenyl)-1,2,4-triazine), hydrazone derivatives (for example, 4-diethylaminobenzaldehyde-1,1-diphenyl hydrazone), quinazoline derivatives (for example, 2-phenyl-4-styryl-quinazoline), benzofuran derivatives (for example, 6-hydroxy-2,3-di(p-methoxyphenyl)benzofuran), α-stilbene derivatives (for example, p-(2,2-diphenylvinyl)-N,N-diphenyl aniline), enamine derivatives, carbazole derivatives (for example, N-ethylcarbazole), and poly-N-vinylcarbazole and derivatives thereof; electron transport materials such as quinone compounds (for example, chloranil and bromoanthraquinone), tetracyanoquinodimethane compounds, fluorenone compounds (for example, 2,4,7-trinitrofluorenone and 2,4,5,7-tetranitro-9-fluorenone), xanthone compounds, and thiophene compounds; and polymers having a group which includes the above-mentioned compounds in the main chain or a side chain thereof. As the charge transport material, these examples may be used alone or in a combination of two or more kinds.

Among these, compounds represented by Formulae (B-1) to (B-3) below are preferable from the viewpoint of charge mobility.

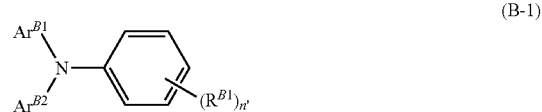

(B-1)

In Formula (B-1), $R^{B1}$ represents a hydrogen atom or a methyl group; and n' represents 1 or 2. In addition, $Ar^{B1}$ and $Ar^{B2}$ represent a substituted or unsubstituted aryl group, and examples of a substituent thereof include a halogen atom, an alkyl group having from 1 to 5 carbon atoms, an alkoxy group having from 1 to 5 carbon atoms, or a substituted amino group which is substituted with an alkyl group having from 1 to 3 carbon atoms.

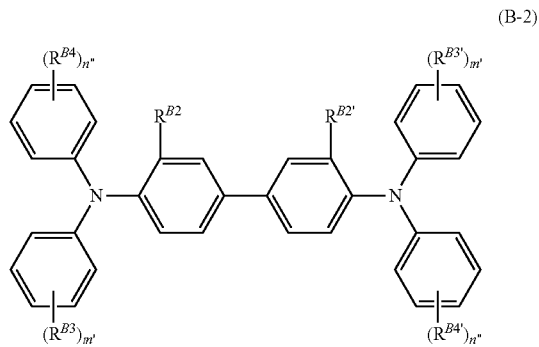

(B-2)

In Formula (B-2), $R^{B2}$ and $R^{B2'}$ each independently represent a hydrogen atom, a halogen atom, an alkyl group having from 1 to 5 carbon atoms, or an alkoxy group having from 1 to 5 carbon atoms. $R^{B3}$, $R^{B3'}$, $R^{B4}$, and $R^{B4'}$ each independently represent a halogen atom, an alkyl group having from 1 to 5 carbon atoms, an alkoxy group having from 1 to 5 carbon atoms, an amino group which is substituted with an alkyl group having from 1 or 2 carbon atoms, a substituted or unsubstituted aryl group, or —C($R^{B5}$)=C($R^{B6}$)($R^{B7}$); and $R^{B5}$, $R^{B6}$, and $R^{B7}$ represent a hydrogen atom, a substituted or unsubstituted alkyl group, or a substituted or unsubstituted aryl group. In addition, m' and n" each independently represent an integer of 0 to 2.

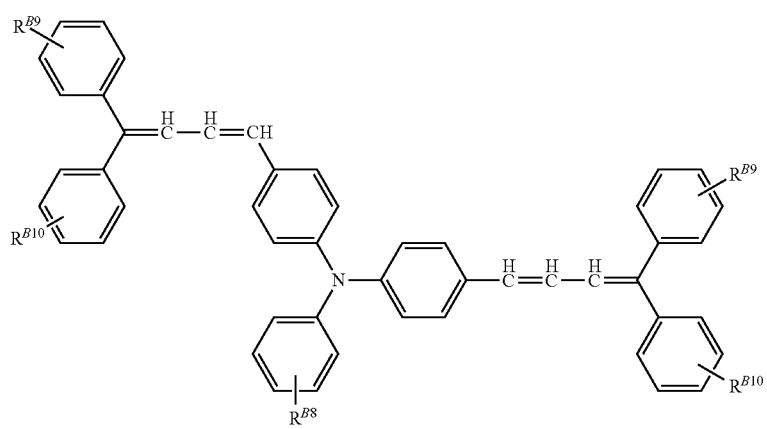

(B-3)

In Formula (B-3), $R^{B8}$ represents a hydrogen atom, an alkyl group having from 1 to 5 carbon atoms, an alkoxy group having from 1 to 5 carbon atoms, a substituted or unsubstituted aryl group, or —CH=CH—CH=C($Ar^{B3}$)$_2$. $Ar^{B3}$ represents a substituted or unsubstituted aryl group. $R^{B9}$ and $R^{B10}$ each independently represent a hydrogen atom, a halogen atom, an alkyl group having from 1 to 5 carbon atoms, an alkoxy group having from 1 to 5 carbon atoms, an amino group which is substituted with an alkyl group having from 1 or 2 carbon atoms, or a substituted or unsubstituted aryl group.

Examples of the binder resin constituting the charge transport layer include insulating resins e.g., a polycarbonate resin such as a polybisphenol-A carbonate and a polybisphenol-Z carbonate, acrylic resins, methacrylic resins, polyarylate resins, polyester resins, polyvinyl chloride resins, polystyrene resins, acrylonitrile-styrene copolymer resins, acrylonitrile-butadiene copolymer resins, polyvinyl acetate resins, polyvinyl formal resins, polysulfone resins, styrene-butadiene copolymer resins, vinylidene chloride-acrylonitrile copolymer resins, vinyl chloride-vinyl acetate-maleic anhydride resins, silicone resins, phenol-formaldehyde resins, polyacrylamide resins, polyamide resins, and chlorinated rubber; and organic photoconductive polymers such as polyvinyl carbazole, polyvinyl anthracene, and polyvinyl pyrene. These binder resins may be used singly or in mixture of two or more types.

The blending ratio of the charge transport material to the binder resin is, for example, preferably from 10:1 to 1:5.

The charge transport layer is formed using a coating liquid for charge transport layer formation in which the above components are added to a solvent.

As a method of dispersing the particles (for example, fluorine resin particles) in the coating liquid for charge transport layer formation, a media disperser such as a ball mill, a vibrating ball mill, an attritor, a sand mill, or a horizontal sand mill, or a media-less disperser such as a stirrer, an ultrasonic disperser, a roll mill, or a high-pressure homogenizer is used. Examples of the high-pressure homogenizer include a collision-type homogenizer in which a dispersion is dispersed under high pressure by liquid-liquid collision or liquid-wall collision, and a penetration-type homogenizer in which a dispersion is dispersed by allowing it to penetrate through a minute channel under high pressure.

As a method of coating the charge generation layer with the coating liquid for charge transport layer formation, a general method is used such as a dipping coating method, an extrusion coating method, a wire bar coating method, a spray coating method, a blade coating method, a knife coating method, or a curtain coating method.

The thickness of the charge transport layer is preferably set to from 5 μm to 50 μm, and more preferably from 10 μm to 40 μm.

Surface Protective Layer

A surface protective layer is the outermost surface layer which is provided on the photosensitive layer. Specifically, the surface protective layer is a curable layer formed of a composition which includes a reactive charge transport material, fluororesin particles, and the additive for an electrophotographic photoreceptor represented by Formula (I).

That is, the surface protective layer is a curable layer having a charge transport function which includes a polymer (or cross-linking substance) of reactive charge transport materials, fluororesin particles, and the additive for an electrophotographic photoreceptor represented by Formula (I).

Furthermore, when the additive for an electrophotographic photoreceptor represented by Formula (I) has a reactive group, the surface protective layer is a curable layer having a charge transport function which includes a polymer (or cross-linking substance) of reactive charge transport materials, fluororesin particles, and a polymer (or cross-linking substance) of a reactive charge transport material and the additive for an electrophotographic photoreceptor represented by Formula (I). In this case, the surface protective layer may include a polymer (cross-linking substance) of the additives for an electrophotographic photoreceptor represented by Formula (I) and an unreacted additive for an electrophotographic photoreceptor represented by Formula (I).

The reactive charge transport material will be described.

It is preferable that the reactive charge transport material be at least one kind of charge transport material having at least one substituent selected from —OH, —OCH$_3$, —NH$_2$, —SH, —COOH, and a group having a functional group which contains a carbon double bond. In particular, as the reactive charge transport material, the charge transport material has preferably at least two (more preferably at least three) substituents selected from —OH, —OCH$_3$, —NH$_2$, —SH, —COOH, and a group having a functional group which contains a carbon double bond. In this way, when the charge transport material includes more of the reactive functional groups (the substituents), the crosslink density increases and a curable layer (cross-linked layer) with a higher strength may be obtained.

It is preferable that the reactive charge transport material be a compound represented by Formula (C) below, from the viewpoint of suppressing the abrasion of a foreign substance removal member or the abrasion of an electrophotographic photoreceptor.

Fr-(D)$_{n3}$    Formula (C)

In Formula (C), Fr represents an organic group (charge transport structure) derived from a compound having a charge transport function; D represents —(—R$^{11}$—Z)$_{n1}$(R$^{12}$)$_{n2}$—Y (in which R$^{11}$ and R$^{12}$ each independently represent a linear or branched alkylene group having from 1 to 5 carbon atoms, Z represents an oxygen atom, NH, or a sulfur atom, Y represents —OH, —OCH$_3$, —NH$_2$, —SH, or —COOH, n1 represents 0 or 1, and n2 represents 0 or 1) or a group having a functional group which contains a carbon double bond; and n3 represents an integer of 1 to 4.

Examples of the group having a functional group which contains a carbon double bond represented by D include groups having at least one selected from an acryloyl group, a methacryloyl group, a styryl group (a vinyl phenyl group), an allyl group, a vinyl group, a vinyl ether group, an allyl vinyl ether group, and derivatives thereof (in particular, groups having at least one selected therefrom in a terminal).

In Formula (C), as the compound having a charge transport function of "the organic group derived from a compound having a charge transport function" represented by Fr, for example, arylamine derivatives are preferable. Examples of the arylamine derivatives include triphenylamine derivatives and tetraphenylbenzidine derivatives.

It is preferable that the compound represented by Formula (C) be a compound represented by Formula (C-1) below. The compound represented by Formula (C-1) is particularly superior in terms of charge mobility, stability to, for example, oxidation, and the like.

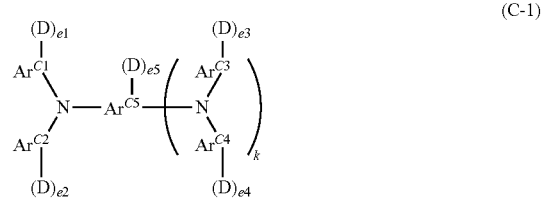

(C-1)

In Formula (C-1), Ar$^{C1}$, Ar$^{C2}$, Ar$^{C3}$, and Ar$^{C4}$ each independently represent a substituted or unsubstituted aryl group and may be the same as or different from each other.

Ar$^{C5}$ represents a substituted or unsubstituted aryl group or a substituted or unsubstituted arylene group.

D represents —(—R$^{11}$—Z)$_{n1}$(R$^{12}$)$_{n2}$—Y (in which R$^{11}$ and R$^{12}$ each independently represent a linear or branched alkylene group having from 1 to 5 carbon atoms, Z represents an oxygen atom, NH, or a sulfur atom, Y represents —OH, —OCH$_3$, —NH$_2$, —SH, or —COOH, n1 represents 0 or 1, and n2 represents 0 or 1) or —(CH$_2$)$_d$—(O—CH$_2$—CH$_2$)$_e$—O—CO—C(R')=CH$_2$ (in which R' represents a hydrogen atom or a methyl group, d represents an integer of 1 to 5, and e represents 0 or 1). e1 to e5 each independently represent 0 or 1 and the total number of "D"s is from 1 to 4. k represents 0 or 1.

Regarding Ar$^{C1}$ to Ar$^{C5}$, examples of a substituent of the substituted aryl group and the substituted arylene group other than D include an alkyl group having from 1 to 4 carbon atoms, an alkoxy group having from 1 to 4 carbon atoms, or a substituted or unsubstituted aryl group having from 6 to 10 carbon atoms.

In Formula (C-1), when D represents "—(—R$^{11}$—Z)$_{n1}$ (R$^{12}$)$_{n2}$—Y", R$^{11}$ and R$^{12}$ each independently represent a linear or branched alkylene group having from 1 to 5 carbon atoms, n1 preferably represents 1, n2 preferably represents 1, and Z preferably represents an oxygen atom.

In Formula (C-1), the total number of "D"s corresponds to n3 in the Formula (C), which is preferably from 2 to 4 and more preferably 3 or 4. When the total number of "D"s is from 2 to 4 and preferably 3 or 4 in a single molecule, the crosslink density increases and a cross-linked layer with a higher strength may be obtained.

In Formula (C-1), it is preferable that Ar$^{C1}$, Ar$^{C2}$, Ar$^{C3}$, and Ar$^{C4}$ represent any one of compounds represented by Formulae (1) to (7) below. In Formulae (1) and (7) below, "-(D)$_e$"s which may be respectively linked to the Ar$^{C1}$, Ar$^{C2}$, Ar$^{C3}$, and Ar$^{C4}$, are also shown (in which e represents any one of e1 to e5).

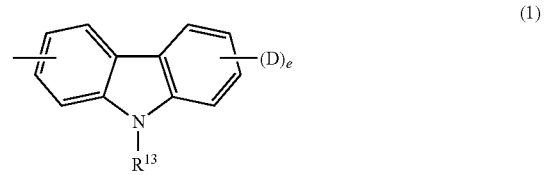

(1)

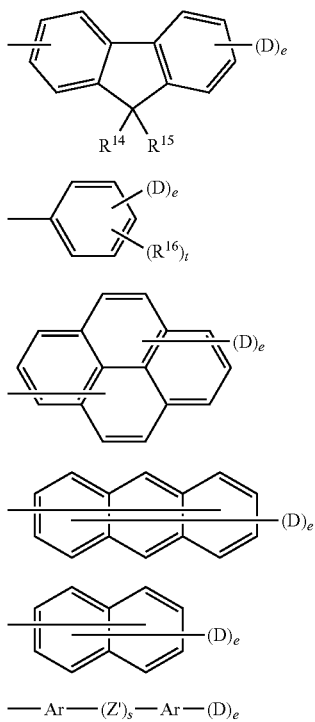

(2)

(3)

(4)

(5)

(6)

(7)

—Ar—(Z')$_s$—Ar—(D)$_e$

In Formulae (1) to (7), $R^{13}$ represents one kind selected from a group consisting of a hydrogen atom, an alkyl group having from 1 to 4 carbon atoms, a phenyl group which may be substituted with an alkyl group having from 1 to 4 carbon atoms or an alkoxy group having from 1 to 4 carbon atoms, an unsubstituted phenyl group, and an aralkyl group having from 7 to 10 carbon atoms; $R^{14}$, $R^{15}$, and $R^{16}$ each independently represent one kind selected from a group consisting of a hydrogen atom, an alkyl group having from 1 to 4 carbon atoms, an alkoxy group having from 1 to 4 carbon atoms, a phenyl group which is substituted with an alkoxy group having from 1 to 4 carbon atoms, an unsubstituted phenyl group, an aralkyl group having from 7 to 10 carbon atoms, and a halogen atom; Ar represents a substituted or unsubstituted arylene group; D and e represent the same as that represented by "D" and "e1 to e5" in Formula (C-1); s represents 0 or 1; and t represents an integer of 1 to 3.

In this case, it is preferable that Ar in Formula (7) be represented by Formula (8) or (9) below.

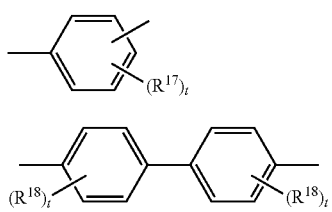

(8)

(9)

In Formula (8) or (9), $R^{17}$ and $R^{18}$ each independently represent one kind selected from a group consisting of a hydrogen atom, an alkyl group having from 1 to 4 carbon atoms, an alkoxy group having from 1 to 4 carbon atoms, a phenyl group which is substituted with an alkoxy group having from 1 to 4 carbon atoms, an unsubstituted phenyl group, an aralkyl group having from 7 to 10 carbon atoms, and a halogen atom; and t represents an integer of 1 to 3.

In addition, it is preferable that Z' in Formula (7) represent any one of compounds represented by Formulae (10) to (17) below.

—(CH$_2$)$_q$— (10)

—(CH$_2$CH$_2$O)$_r$— (11)

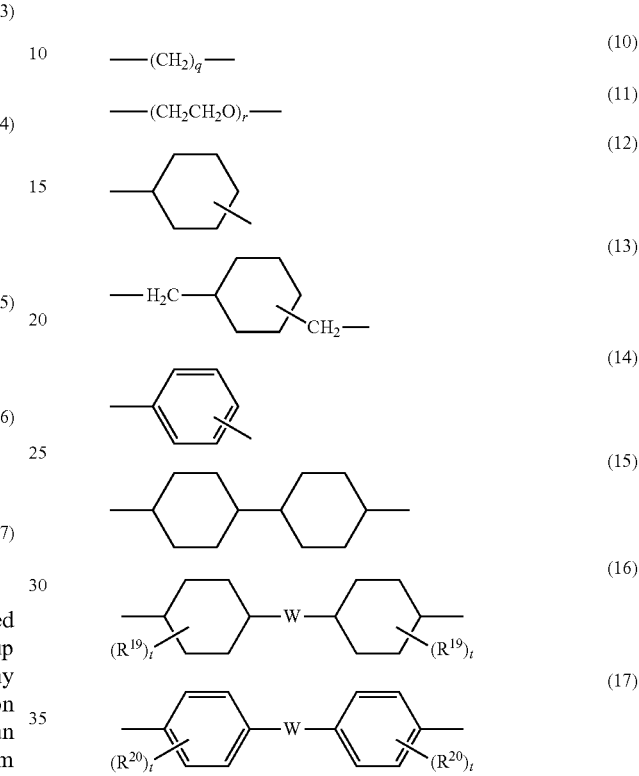

(12)

(13)

(14)

(15)

(16)

(17)

In Formulae (10) to (17), $R^{19}$ and $R^{20}$ each independently represent one kind selected from a group consisting of a hydrogen atom, an alkyl group having from 1 to 4 carbon atoms, an alkoxy group having from 1 to 4 carbon atoms, a phenyl group which is substituted with an alkoxy group having from 1 to 4 carbon atoms, an unsubstituted phenyl group, an aralkyl group having from 7 to 10 carbon atoms, and a halogen atom; W represents a divalent group; q and r each independently represent an integer of 1 to 10; and "t"s each independently represent an integer of 1 to 3.

It is preferable that W in Formulae (16) and (17) represent any one of divalent groups represented by Formulae (18) to (26) below. In this case, in Formula (25), u represents an integer of 0 to 3.

—CH$_2$— (18)

—C(CH$_3$)$_2$— (19)

—O— (20)

—S— (21)

—C(CF$_3$)$_2$— (22)

—Si(CH$_3$)$_2$— (23)

-continued

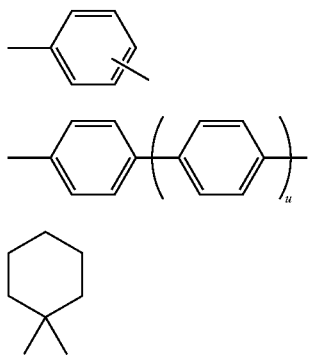
(24)

(25)

(26)

In Formula (C-1), it is preferable that, when k is 0, $Ar^{C5}$ represent any one of aryl groups represented by Formulae (1) to (7), which is used as an example in the description of $Ar^{C1}$ to $Ar^{C4}$; and when k is 1, $Ar^{C5}$ represent an arylene group in which a hydrogen atom is excluded from any one of aryl groups represented by Formulae (1) to (7).

Specific examples of the compound represented by Formula (C-1) include compounds disclosed in JP-A-2011-175038 and JP-A-2011-112801.

Regarding the content of the reactive charge transport material, for example, the solid content concentration thereof in a coating solution is preferably greater than or equal to 80% by weight, more preferably greater than or equal to 90% by weight, and still more preferably greater than or equal to 95% by weight, with respect to all of the components of the layer (in terms of solid content) other than fluororesin particles and a fluorinated alkyl group-containing copolymer. When the solid content concentration is less than 90% by weight, electrical characteristics may deteriorate.

Next, the fluororesin particles will be described.

The fluororesin particles are not particularly limited, but examples thereof include particles of polytetrafluoroethylene, perfluoroalkoxy fluororesin, polychlorotrifluoroethylene, polyvinylidene fluoride, polydichlorodifluoroethylene, tetrafluoroethylene-perfluoroalkylvinylether copolymer, tetrafluoroethylene-hexafluoropropylene copolymer, tetrafluoroethylene-ethylene copolymer, and tetrafluoroethylene-hexafluoropropylene-perfluoroalkylvinylether copolymer.

As the fluororesin particles, these examples may be used alone or in a combination of two or more kinds.

It is preferable that the weight average molecular weight of the fluororesin which forms the fluororesin particles be, for example, from 3,000 to 5,000,000.

The average primary particle size of the fluororesin particles is, for example, preferably from 0.01 μm to 10 μm and more preferably from 0.05 μm to 2.0 μm.

In this case, the average primary particle size of the fluororesin particles represents a value which is obtained by measuring a measurement solution diluted with the same solvent as a dispersion in which the fluororesin particles are dispersed, at a refractive index of 1.35 using a laser diffraction particle size analyzer LA-700 (manufactured by HORIBA Ltd.).

Examples of commercially available products of the fluororesin particles include LUBRON series (manufactured by DAIKIN INDUSTRIES Ltd.), Teflon (registered trademark) series (manufactured by E. I. du Pont de Nemours and Company), and Dyneon series (manufactured by Sumitomo 3M Ltd.).

The content of the fluororesin particles is, for example, preferably from 1% by weight to 30% by weight and more preferably from 2% by weight to 20% by weight, with respect to all of the components of the layer (in terms of solid content).

The fluororesin particles may be used in combination with an alkyl fluoride group-containing copolymer as a dispersing aid (also called "a dispersant").

For example, examples of the alkyl fluoride group-containing copolymer include alkyl fluoride group-containing copolymers having any one of repeating units represented by Structural Formulae (E) and (F) below.

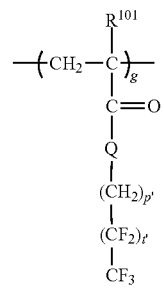

Structural Formula (E)

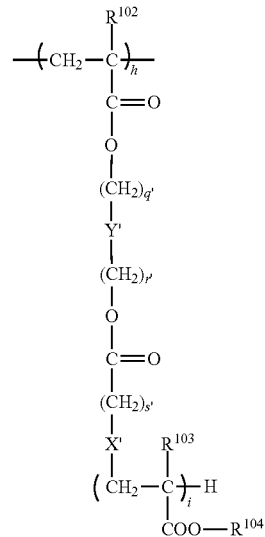

Structural Formula (F)

In Structural Formulae (E) and (F), $R^{101}$, $R^{102}$, $R^{103}$, and $R^{104}$ each independently represent a hydrogen atom or an alkyl group. X' represents an alkylene chain, a halogen-substituted alkylene chain, —S—, —O—, —NH—, or a single bond. Y' represents an alkylene chain, a halogen-substituted alkylene chain, —($C_zH_{2z-1}$(OH))—, or a single bond, in which z represents an integer of 1 or more. Q represents —O— or —NH—. g, h, and i each independently represent an integer of 1 or more. p', q', r', and s' each independently represent 0 or an integer of 1 or more. t' represents an integer of 1 to 7.

In Structural Formulae (E) and (F), as the groups represented by $R^{101}$, $R^{102}$, $R^{103}$, and $R^{104}$, a hydrogen atom, a methyl group, or an ethyl group is preferable and a methyl group is more preferable.

It is preferable that the alkylene chains represented by X' and Y' (an unsubstituted alkylene chain and a halogen-substituted alkylene chain) be an alkylene chain having from 1 to 10 carbon atoms.

In —($C_zH_{2z-1}$(OH))— represented by Y', it is preferable that z represent an integer of 1 to 10.

It is preferable that p', q', r', and s' each independently represent 0 or an integer of 1 to 10.

In the alkyl fluoride group-containing copolymer, the ratio of content of Structural Formula (E) and Structural Formula (F), that is, g:h is preferably from 1:9 to 9:1 and more preferably 3:7 to 7:3.

The alkyl fluoride group-containing copolymer may further include a repeating unit represented by Structural Formula (G). The ratio of the total content of Structural Formula (E) and Structural Formula (F) to the content of Structural Formula (G), that is, g+h:j is preferably from 10:0 to 7:3 and more preferably from 9:1 to 7:3.

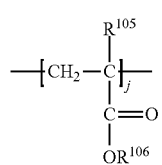

Structural Formula (G)

In Structural Formula (G), $R^{105}$ and $R^{106}$ represent a hydrogen atom or an alkyl group. j represents an integer of 1 or more.

As the groups represented by $R^{105}$ and $R^{106}$, a hydrogen atom, a methyl group, and an ethyl group are preferable and a methyl group is more preferable.

Examples of commercially available products of the alkyl fluoride group-containing copolymer include GF-300 and GF-400 (manufactured by TOAGOSEI CO., LTD.); SURFLON series (manufactured by AGC SEIMI CHEMICAL CO., LTD.); FTERGENT series (manufactured by NEOS COMPANY LIMITED); PF series (manufactured by KITAMURA CHEMICALS CO., LTD.); MEGAFACE series (manufactured by DIC Corporation); and FC series (manufactured by 3M Company).

As the alkyl fluoride group-containing copolymer, these examples may be used alone or in a combination of two or more kinds.

The weight average molecular weight of the alkyl fluoride group-containing copolymer is preferably from 2,000 to 250,000 and more preferably from 3,000 to 150,000.

The weight average molecular weight of the alkyl fluoride group-containing copolymer is measured using gel permeation chromatography (GPC).

The content of the alkyl fluoride group-containing copolymer is, for example, preferably from 0.5% by weight to 10% by weight and more preferably from 1% by weight to 7% by weight, with respect to the weight of the fluororesin particles.

Hereinafter, the surface protective layer will be described in further detail.

In the surface protective layer, the reactive charge transport material (for example, a compound represented by Formula (C)) may be used in combination with a phenol resin, a urea resin, an alkyd resin, or the like. In addition, in order to improve strength, it is also effective that a compound having more functional groups in a single molecule such as spiroacetal guanamine resin (for example, "CTU-guanamine" (manufactured by Ajinomoto Fine Techno Co., Inc.)) be copolymerized with a material in the cross-linking substance.

In order to efficiently suppress the oxidation due to discharge gas, another thermo-setting resin such as phenol resin may be added and mixed into the surface protective layer so as not to be excessively adsorbed to the surface protective layer.

An antioxidant may be added to the surface protective layer. The antioxidant is an additive used for suppressing a deterioration due to oxidized gas such as ozone which is generated from a charging device.

Examples of the antioxidant include well-known antioxidants such as hindered phenol antioxidants, aromatic amine antioxidants, hindered amine antioxidants, organic sulfur antioxidants, phosphate antioxidants, dithiocarbamate antioxidants, thiourea antioxidants, and benzimidazole antioxidants.

It is preferable that a surfactant be added to the surface protective layer. The surfactant is not particularly limited as long as it includes fluorine atoms and at least one structure of an alkylene oxide structure and a silicone structure, but the surfactant having the plural above-described structures is preferable because the affinity to and the solubility in a charge transport organic compound are high, the layer forming property of a surface-protective-layer-forming coating solution is improved, and wrinkles and unevenness in the surface protective layer are suppressed.

In the surface protective layer, a coupling agent or a fluorine compound may be used in order to adjust the film forming property, the flexibility, the lubricity, the adhesion, and the like of a layer. As such a compound, various coupling agents and commercially available silicone hard-coating agents are used.

A resin which is soluble in alcohol may be added to the surface protective layer, for the purposes of resistance to discharge gas, mechanical strength, scratch resistance, particle dispersibility, viscosity control, torque reduction, wear amount control, an increase in pot life (the preservability of a layer-forming coating solution), and the like.

In this case, the resin which is soluble in alcohol indicates a resin of which 1% by weight or greater is soluble in an alcohol having from 5 or less carbon atoms. Examples of the resin which is soluble in alcohol include polyvinyl acetal resin and polyvinyl phenol resin.

Various particles may be added to the surface protective layer in order to lower residual potential or to improve strength. An example of the particles includes silicon-containing particles. The silicon-containing particles include silicon atoms as a component, and specific examples thereof include colloidal silica particles and silicone particles.

For the same purpose, oil such as silicone oil may be added to the surface protective layer.

Metal, metal oxide, carbon black, or the like may be added to the surface protective layer.

It is preferable that the surface protective layer be a curable layer (cross-linked layer) in which the reactive charge transport materials are polymerized (cross-linked) using an acid catalyst. Examples of the acid catalyst include aliphatic carboxylic acids such as acetic acid, chloroacetic acid, trichloroacetic acid, trifluoroacetic acid, oxalic acid, maleic acid, malonic acid, and lactic acid; aromatic carboxylic acids such as benzoic acid, phthalic acid, terephthalic acid, and trimellitic acid; and aliphatic and aromatic sulfonic acids such as methanesulfonic acid, dodecylsulfonic acid, benzenesulfonic acid, dodecylbenzenesulfonic acid, and naphthalenesulfonic acid. Among these, a sulfur-containing material is preferable.

In this case, the content of the catalyst is preferably from 0.1% by weight to 50% by weight and more preferably from 10% by weight to 30% by weight, with respect to all of the components of the layer (in terms of solid content) other than fluororesin particles and the fluorinated alkyl group-containing copolymer. When the content is less than the above-described range, catalytic activity is too low, and when the content is greater than the above-described range, lightfastness may deteriorate. Lightfastness indicates a phenomenon in which, when the photosensitive layer is exposed to light emitted from the outside such as room illumination, the density of an exposed portion is reduced. The reason is not clear but it is presumed that the same phenomenon as an optical memory effect disclosed in JP-A-5-099737 occurs.

The surface protective layer with the above-described configuration is formed using a surface-protective-layer-forming coating solution into which the above-described components are mixed. The surface-protective-layer-forming coating solution may be prepared without a solvent, and optionally, may be prepared with a solvent. As such a solvent, one kind or a mixture of two or more kinds may be used, in which the boiling point thereof is preferably less than or equal to 100° C. As the solvent, a solvent having at least one hydroxyl group (for example, alcohols) is particularly preferable.

In addition, when the coating solution is formed by a reaction of the above-described components, the components may be simply mixed and dissolved in the solvent, but may be heated at room temperature (for example, 25° C.) to 100° C. and preferably 30° C. to 80° C. for 10 minutes to 100 hours and preferably 1 hour to 50 hours. In addition, at this time, it is preferable that ultrasonic waves be applied thereto. As a result, a partial reaction may advance and thus a layer with less defects and less unevenness in thickness may be obtained.

The surface-protective-layer-forming coating solution is coated according to a well-known method such as a blade coating method, a wire-bar coating method, a spray coating method, a dip coating method, a bead coating method, an air knife coating method, or a curtain coating method, and optionally heated at a temperature of, for example, 100° C. to 170° C. to be cured. As a result, the protective surface layer is obtained.

The thickness of the surface protective layer is preferably from 1 μm to 15 μm and more preferably from 3 μm to 10 μm.

As described above, an example of the functional separation-type electrophotographic photoreceptor has been described, however, for example, when the single layer-type photosensitive layer (charge generation/charge transport layer) shown in FIG. 3 is formed, the content of the charge generation material is preferably from about 10% by weight to about 85% by weight, and more preferably from 20% by weight to 50% by weight. In addition, the content of the charge transport material is preferably from 5% by weight to 50% by weight.

A method of forming the single layer-type photosensitive layer is the same as the method of forming the charge generation layer or the charge transport layer. The thickness of the single layer-type photosensitive layer is preferably from about 5 μm to about 50 μm, and more preferably from 10 μm to 40 μm.

Image Forming Apparatus, Process Cartridge

An image forming apparatus according to this exemplary embodiment may include the electrophotographic photoreceptor according to this exemplary embodiment, a charging unit that charges a surface of the electrophotographic photoreceptor, a latent image forming unit that forms an electrostatic latent image on a charged surface of the electrophotographic photoreceptor, a developing unit that develops the electrostatic latent image formed on the surface of the electrophotographic photoreceptor with a toner to form a toner image, and a transfer unit that transfers the toner image formed on the surface of the electrophotographic photoreceptor onto a recording medium.

A process cartridge according to this exemplary embodiment may include the electrophotographic photoreceptor according to this exemplary embodiment, and a cleaning unit that cleans the electrophotographic photoreceptor.

Figure 4:
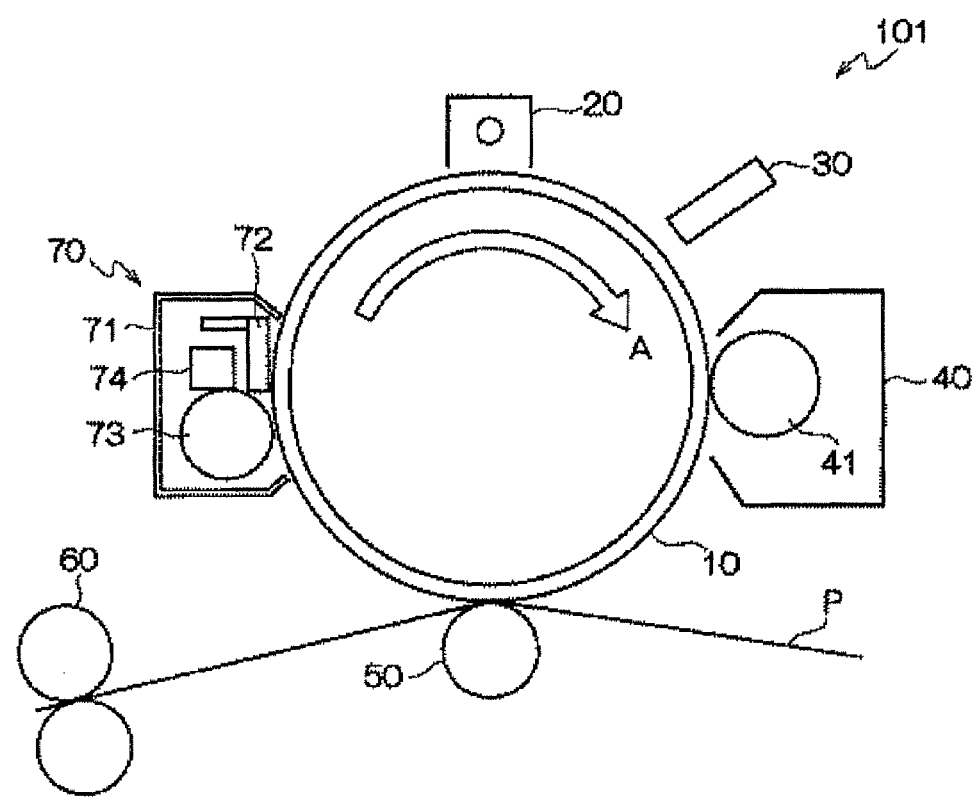
FIG. 4 is a diagram schematically illustrating a configuration of an image forming apparatus according to an exemplary embodiment of the invention.

FIG. 4 is a diagram schematically showing the configuration of an image forming apparatus according to this exemplary embodiment.

As shown in FIG. 4, an image forming apparatus 101 according to this exemplary embodiment is provided with, for example, an electrophotographic photoreceptor 10 that rotates in a clockwise direction as shown by the arrow A, a charging device 20 (an example of charging unit) that is provided above the electrophotographic photoreceptor 10 to face the electrophotographic photoreceptor 10 and to charge a surface of the electrophotographic photoreceptor 10, an exposure device 30 (an example of electrostatic latent image forming unit) that exposes the surface of the electrophotographic photoreceptor 10 charged by the charging device 20 to form an electrostatic latent image, a developing device 40 (an example of developing unit) that adheres a toner contained in a developer to the electrostatic latent image formed using the exposure device 30 to form a toner image on the surface of the electrophotographic photoreceptor 10, a transfer device 50 that causes recording paper P (transfer medium) to be charged with a polarity different from the charging polarity of the toner to transfer the toner image on the electrophotographic photoreceptor 10 onto the recording paper P, and a cleaning device 70 (an example of toner removing unit) that cleans the surface of the electrophotographic photoreceptor 10. In addition, a fixing device 60 is provided to fix the toner image while transporting the recording paper P with the toner image formed thereon.

Hereinafter, the major constituent members in the image forming apparatus 101 according to this exemplary embodiment will be described in detail.

Charging Device

Examples of the charging device 20 include contact-type charging units using a conductive charging roller, a charging brush, a charging film, a charging rubber blade, a charging tube, and the like. In addition, examples of the charging device 20 also include well-known charging units such as non-contact-type roller charging units, and scorotron charging units and corotron charging units using corona discharge. A contact-type charging unit is preferable as the charging device 20.

Exposure Device

Examples of the exposure device 30 include optical equipment that exposes the surface of the electrophotographic photoreceptor 10 with light such as semiconductor laser light, LED light, or liquid crystal shutter light in the form of an image. The wavelength of a light source is preferably in the spectral sensitivity region of the electrophotographic photoreceptor 10. As for the wavelength of the semiconductor laser, for example, a near-infrared laser having an oscillation wavelength of approximately 780 nm may be preferably used. However, the wavelength is not limited thereto, and a laser having an oscillation wavelength of 600 nm to less than 700 nm or a laser having an oscillation wavelength of 400 nm to 450 nm as a blue laser may also be used. In addition, as the exposure device 30, it is also effective to use a surface-emitting laser light source that outputs multi-beams in order to form a color image for example.

Developing Device

Examples of the configuration of the developing device 40 include a configuration in which a developing roll 41 arranged in a developing region so as to be opposed to the electrophotographic photoreceptor 10 is provided in a container accommodating a two-component developer formed of a toner and a carrier. The developing device 40 is not particularly limited as long as it performs the development with a two-component developer, and a known configuration is employed.

Here, the developer for use in the developing device 40 will be described.

The developer may be a single-component developer formed of a toner, or may be a two-component developer containing a toner and a carrier.

The toner contains, for example, toner particles containing a binder resin, a colorant, and if necessary, other additives such as a release agent, and if necessary, an external additive.

The average shape factor of the toner particles (a number average of the shape factor represented by the expression: shape factor=$(ML^2/A) \times (\pi/4) \times 100$, where ML represents a maximum length of the particle and A represents a projected area of the particle) is preferably from 100 to 150, more preferably from 105 to 145, and even more preferably from 110 to 140. Furthermore, a volume average particle diameter of the toner is preferably from 3 μm to 12 μm, more preferably from 3.5 μm to 10 μm, and even more preferably from 4 μm to 9 μm.

Although the method of manufacturing the toner particles is not particularly limited, toner particles are used that are manufactured by, for example, a kneading and pulverizing method in which a binder resin, a colorant, a release agent, and if necessary, a charge-controlling agent and the like are added, and the resultant mixture is kneaded, pulverized and classified; a method in which the shapes of the particles obtained using the kneading and pulverizing method are changed by a mechanical impact force or thermal energy; an emulsion polymerization and aggregation method in which polymerizable monomers of a binder resin are subjected to emulsion polymerization, the resultant dispersion formed and a dispersion of a colorant, a release agent, and if necessary, a charge-controlling agent and the like are mixed, aggregated, and heat-melted to obtain toner particles; a suspension polymerization method in which polymerizable monomers for obtaining a binder resin, a colorant, a release agent, and if necessary, a solution of a charge-controlling agent are suspended in an aqueous solvent and polymerization is performed; and a dissolution suspension method in which a binder resin, a colorant, a release agent, and if necessary, a solution of a charge-controlling agent are suspended in an aqueous solvent and granulation is performed.

In addition, a known method such as a manufacturing method in which the toner particles obtained using one of the above methods are used as a core to achieve a core shell structure by further making aggregated particles adhere to the toner particles and by coalescing them with heating is used. As the toner manufacturing method, a suspension polymerization method, an emulsion polymerization and aggregation method, and a dissolution suspension method, all of which are used to manufacture the toner particles using an aqueous solvent, are preferable, and an emulsion polymerization and aggregation method is particularly preferable from the viewpoint of controlling the shape and the particle size distribution.

The toner is manufactured by mixing the above toner particles and the above external additive using a Henschel mixer, a V-blender, or the like. In addition, when the toner particles are manufactured in a wet manner, the external additive may be externally added in a wet manner.

In addition, when the toner is used as a two-component developer, the mixing ratio of the toner to the carrier is set to a known ratio. The carrier is not particularly limited. However, preferable examples of the carrier include a carrier in which the surfaces of magnetic particles are coated with a resin.

Transfer Device

Examples of the transfer device 50 include well-known transfer charging units such as contact-type transfer charging units using a belt, a roller, a film, and a rubber blade, and scorotron transfer charging units and corotron transfer charging units using corona discharge.

Cleaning Device

The cleaning device 70 includes, for example, a housing 71, a cleaning blade 72, and a cleaning brush 73 arranged at the downstream side of the cleaning blade 72 in the rotation direction of the electrophotographic photoreceptor 10. In addition, for example, a lubricant 74 in a solid state is arranged to contact with the cleaning brush 73.

Hereinafter, the operation of the image forming apparatus 101 according to this exemplary embodiment will be described. First, when the electrophotographic photoreceptor 10 is rotated in the direction represented by the arrow A, it is negatively charged by the charging device 20 at the same time.

The electrophotographic photoreceptor 10, the surface of which has been negatively charged by the charging device 20, is exposed using the exposure device 30, and a latent image is formed on the surface thereof.

When a part in the electrophotographic photoreceptor 10, in which the latent image has been formed, approaches the developing device 40, the developing device 40 (developing roll 41) adheres a toner to the latent image to form a toner image.

When the electrophotographic photoreceptor 10 having the toner image formed thereon is further rotated in the direction of the arrow A, the transfer device 50 transfers the toner image onto recording paper P. As a result, the toner image is formed on the recording paper P.

The fixing device 60 fixes the toner image to the recording paper P having the image formed thereon.

Figure 5:
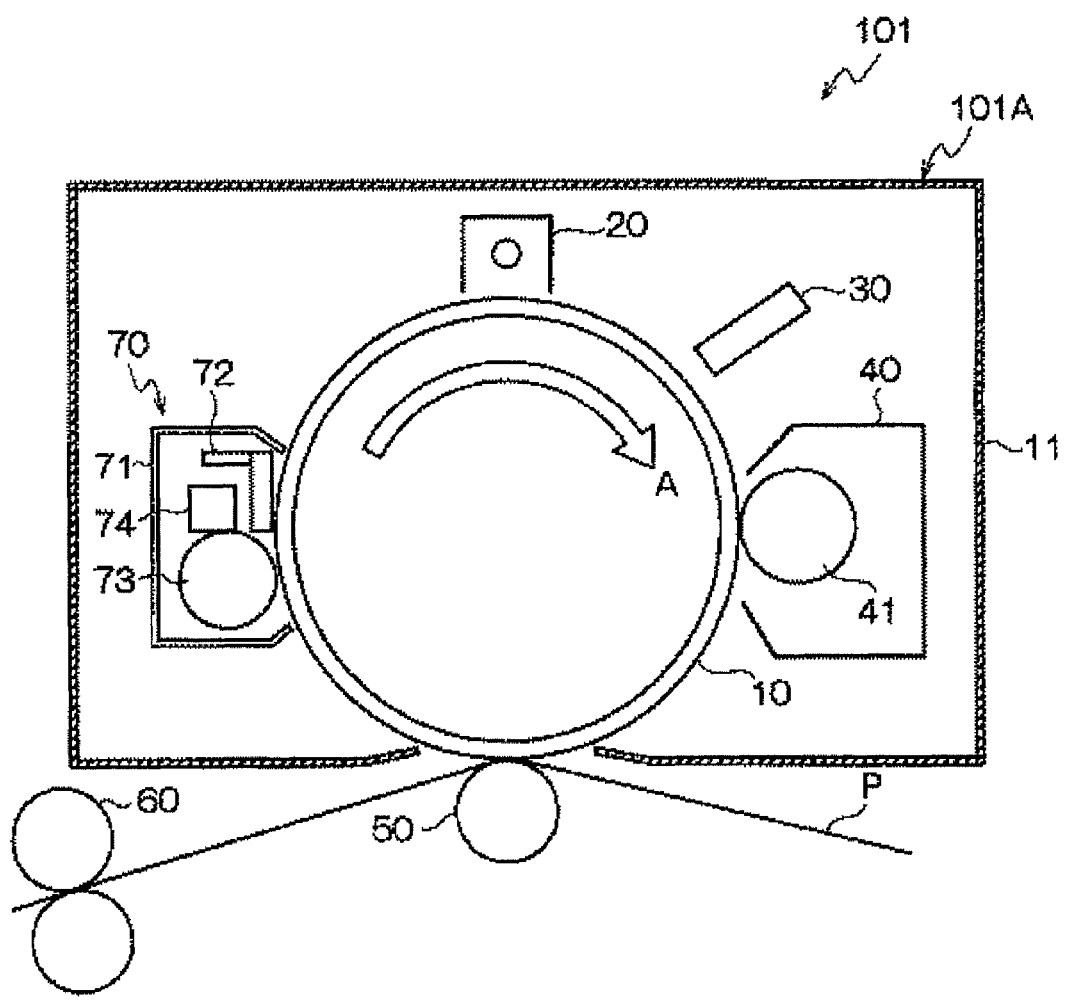
FIG. 5 is a diagram schematically illustrating a configuration of an image forming apparatus according to another exemplary embodiment of the invention.

The image forming apparatus 101 according to this exemplary embodiment may be provided with, for example, a process cartridge 101A that integrally accommodates an electrophotographic photoreceptor 10, a charging device 20, an exposure device 30, a developing device 40, and a cleaning device 70 in a housing 11 as shown in FIG. 5. This process cartridge 101A integrally accommodates plural members and is detachably mounted on the image forming apparatus 101.

The configuration of the process cartridge 101A is not limited thereto. Any configuration is applicable as long as the process cartridge 101A is provided with at least the electrophotographic photoreceptor 10. For example, a configuration may be also applicable in which the process cartridge 101A is provided with at least one selected from the charging device 20, the exposure device 30, the developing device 40, the transfer device 50, and the cleaning device 70.

The image forming apparatus 101 according to this exemplary embodiment is not limited to the above configuration. For example, the image forming apparatus 101 may be provided with a first erasing device, which aligns the polarities of the residual toners to easily remove the residual toners with the cleaning brush, and which is disposed around the electrophotographic photoreceptor 10 at the downstream side of the transfer device 50 in the rotation direction of the electrophotographic photoreceptor 10 and at the upstream side of the cleaning device 70 in the rotation direction of the electrophotographic photoreceptor. The image forming apparatus 101 may also be provided with a second erasing device, which erases charges on the surface of the electrophotographic photoreceptor 10, and which is disposed at the downstream side of the cleaning device 70 in the rotation direction of the electrophotographic photoreceptor and at the upstream side of the charging device 20 in the rotation direction of the electrophotographic photoreceptor.

In addition, the image forming apparatus 101 according to this exemplary embodiment is not limited to the above configuration. For example, a known configuration may be employed such as an intermediate transfer-type image forming apparatus in which a toner image formed on the electrophotographic photoreceptor 10 is transferred onto an intermediate transfer member and is then transferred onto recording paper P or a tandem-type image forming apparatus.

EXAMPLES

The exemplary embodiment will be described in detail using the following Examples, but is not limited thereto.

Hereinafter, "part(s)" represents "part(s) by weight" unless specified otherwise.

Example 1

Synthesis of Compound Represented by Formula (I)

Figure 6:
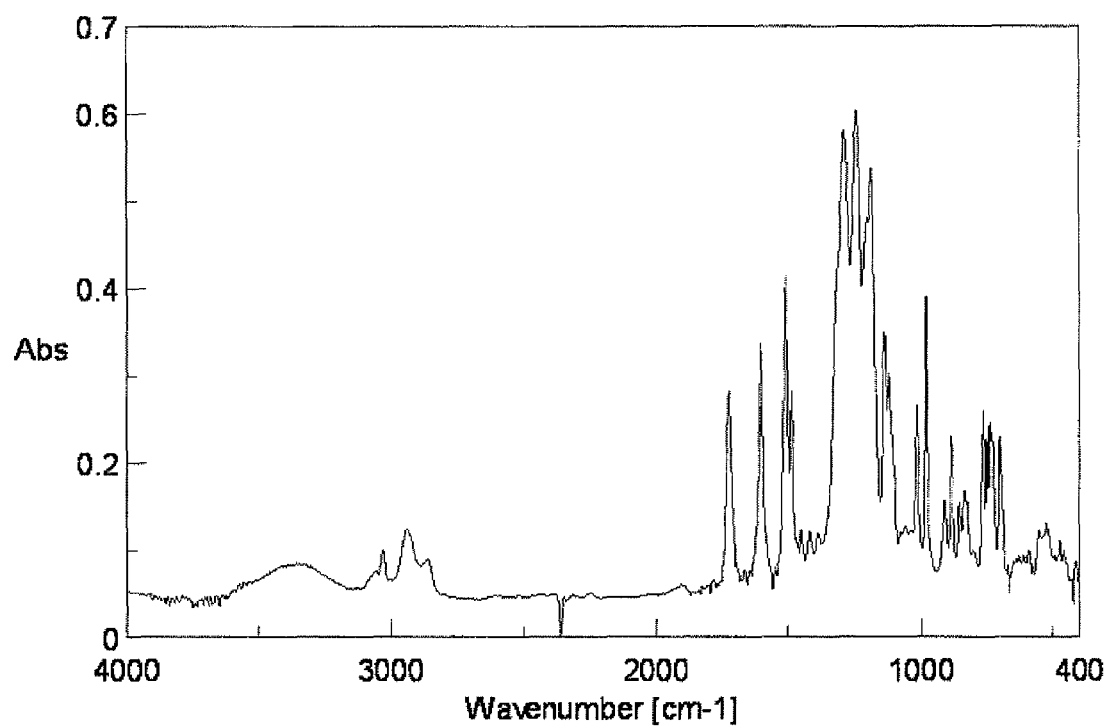
FIG. 6 is the IR spectrum of Compound (I)-8.

5 g of Arylamine compound (A) represented by the following structural formula, 8.6 g of Fluorine-containing hydroxybenzoic acid ester (B) represented by the following structural formula, and 0.1 g of tetrabutoxytitanium are put into a 50 ml flask, followed by reaction in a nitrogen atmosphere at 150° C. for 10 hours. The reaction solution is dissolved in toluene and purified with silica gel column chromatography. As a result, 3.1 g of Compound (I)-8 shown in Table 2 is obtained as colorless oil. The IR spectrum of Compound (I)-8 is shown in FIG. 6.

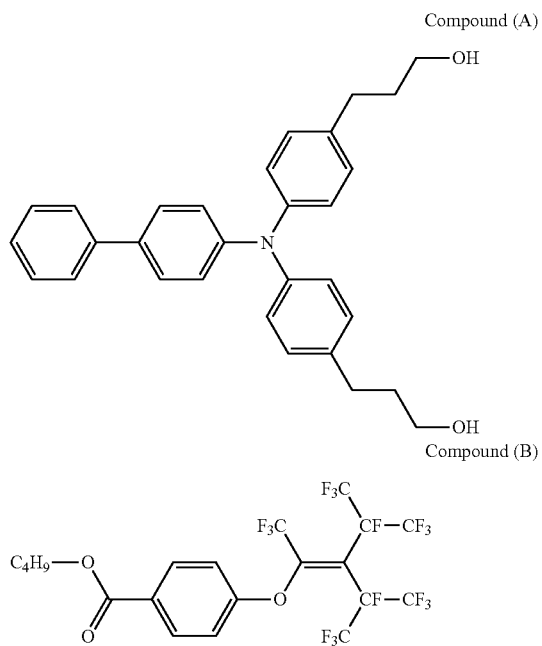

Compound (A)

Compound (B)

Example 2

Synthesis of Compound Represented by Formula (I)

Figure 7:
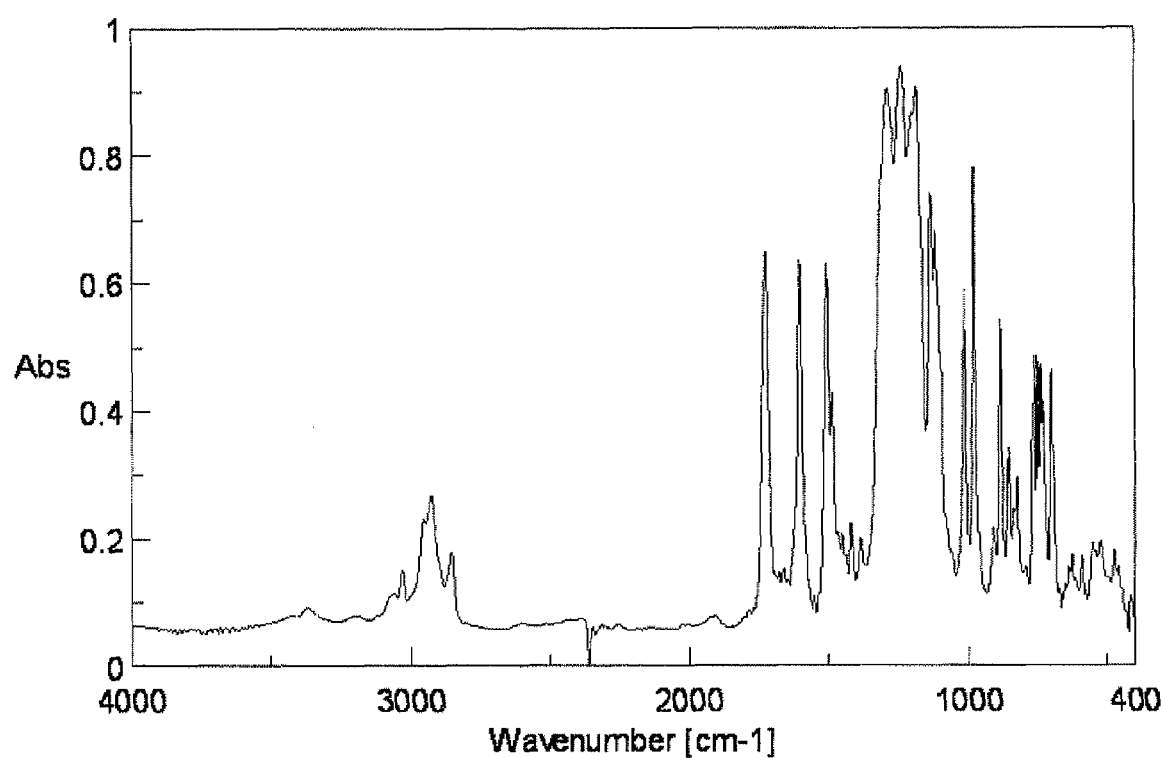
FIG. 7 is the IR spectrum of Compound (I)-7.

5 g of Arylamine compound (A), 20 g of Fluorine-containing hydroxybenzoic acid ester (C) represented by the following structural formula, and 0.1 g of tetrabutoxytitanium are put into a 50 ml flask, followed by reaction in a nitrogen atmosphere at 160° C. for 15 hours. The reaction solution is dissolved in toluene and purified with silica gel column chromatography. As a result, 6.2 g of Compound (I)-7 shown in Table 2 is obtained as colorless oil. The IR spectrum of Compound (I)-7 is shown in FIG. 7.

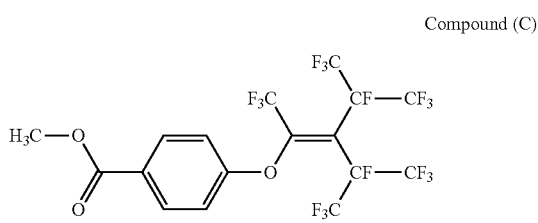

Compound (C)

Example 11

Preparation of Electrophotographic Photoreceptor 1

100 parts of zinc oxide (manufactured by TAYCA CORPORATION, average particle size: 70 nm, specific surface area: 15 m²/g) and 500 parts of tetrahydrofuran are stirred and mixed and 1.2 parts of silane coupling agent (manufactured by Shin-Etsu Chemical Co., Ltd., KBM 502) is added thereto, followed by stirring for 2 hours. Next, tetrahydrofuran is removed by distillation under reduced pressure, followed by baking at 120° C. for 3 hours. As a result, zinc oxide particles with surfaces treated with a silane coupling agent are obtained. 110 parts of zinc oxide particles with the treated surfaces is added to 500 parts of tetrahydrofuran, followed by stirring and mixing. Then, a solution in which 1.5 parts of alizarin is dissolved in 50 parts of tetrahydrofuran is added thereto, followed by stirring at 50° C. for 5 hours. Next, zinc oxide particles with alizarin added are separated through filtration under reduced pressure, followed by drying under reduced pressure at 60° C. As a result, zinc oxide particles with alizarin added are obtained.

60 parts of the obtained zinc oxide particles with alizarin added, 13.5 parts of curing agent (blocked isocyanate, manufactured by Sumitomo Bayer Urethane Co., Ltd., SUMIDUR 3175), and 15 parts of butyral resin (manufactured by SEKISUI CHEMICAL CO. LTD., S-LEC BM-1) are dissolved in 85 parts of methyl ethyl ketone to obtain a solution. 38 parts of the obtained solution and 30 parts of methyl ethyl ketone are mixed, followed by dispersion with a sand mill for 2 hours and 30 minutes using glass beads with a diameter of 1 mm. As a result, a dispersion is obtained. This dispersion is dip-coated on a substrate with a diameter of 84 mm which is a drawn aluminum tube, followed by drying and curing at 170° C. for 40 minutes. As a result, an undercoat layer with a thickness of 22 μm is obtained.

1 part of chlorogallium phthalocyanine having distinct diffraction peaks at Bragg angles (2θ±0.2°) in the X-ray diffraction spectrum of 7.4°, 16.6°, 25.5°, and 28.3°, 1 part of polyvinyl butyral (manufactured by SEKISUI CHEMICAL CO., LTD., S-LEC BM-S), and 100 parts of n-butyl acetate are mixed and dispersed for 1 hour with a paint shaker using glass beads. As a result, a coating solution is obtained. This coating solution is dip-coated on the obtained undercoat layer, followed by heating and drying at 100° C. for 10 minutes. As a result, a charge generation layer with a thickness of 0.15 μm is formed.

2 parts of Compound (D) represented by the following structural formula, 0.2 part of Compound (I)-7 synthesized in Example 2, and 3 parts of polymer (viscosity average molecular weight: 51,000) having continuous Base units 1 below are dissolved in 14 parts of tetrahydrofuran and 6 parts of toluene. Then, 0.4 part of polytetrafluoroethane particles (manufactured by DAIKIN INDUSTRIES Ltd. LUBRON L-2) is dispersed therein with 0.01 part of GF-300 (dispersing aid, manufactured by TOAGOSEI CO., LTD.). As a result, a coating solution is obtained. This coating solution is dip-coated on the obtained charge generation layer, followed by heating at 110° C. for 60 minutes. As a result, a charge transport layer with a thickness of 25 μm is formed. In this way, Electrophotographic photoreceptor-1 is obtained.

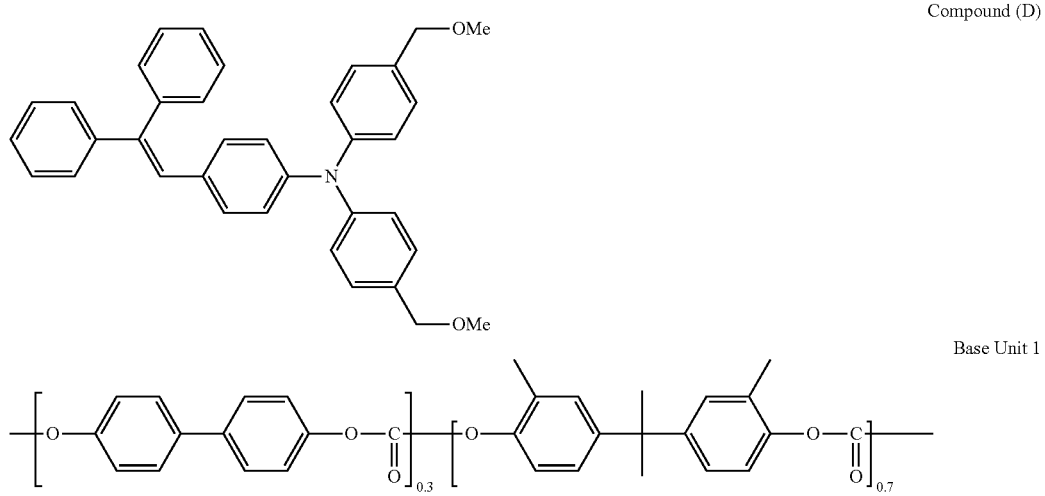

Compound (D)

Base Unit 1

Example 12

Preparation of Electrophotographic Photoreceptor-2

The layers are formed up to the charge transport layer with the same preparation method as that of Electrophotographic photoreceptor-1, except that LUBRON L-2 and GF-300 are not used. In this way, Electrophotographic photoreceptor-2 is obtained.

Example 13

Preparation of Electrophotographic Photoreceptor-3

The layers are formed up to the charge transport layer with the same preparation method as that of Electrophotographic photoreceptor-1, except that Compound (I)-10 shown in Table 3 is used instead of Compound (I)-7. In this way, Electrophotographic photoreceptor-3 is obtained.

Example 14

Preparation of Electrophotographic Photoreceptor-4

The layers are formed up to the charge transport layer with the same preparation method as that of Electrophotographic photoreceptor-1, except that Compound (I)-11 shown in Table 3 is used instead of Compound (I)-7. In this way, Electrophotographic photoreceptor-4 is obtained.

Example 15

Preparation of Electrophotographic Photoreceptor-5

The layers are formed up to the charge transport layer with the same preparation method as that of Electrophotographic photoreceptor-1, except that Compound (I)-27 shown in Table 5 is used instead of Compound (I)-7. In this way, Electrophotographic photoreceptor-5 is obtained.

Example 16

Preparation of Electrophotographic Photoreceptor-6

The layers are formed up to the charge transport layer with the same preparation method as that of Electrophotographic photoreceptor-1, except that Compound (I)-65 shown in Table 6 is used instead of Compound (I)-7. In this way, Electrophotographic photoreceptor-6 is obtained.

Example 17

Preparation of Electrophotographic Photoreceptor-7

The layers are formed up to the charge transport layer with the same preparation method as that of Electrophotographic photoreceptor-1, except that Compound (I)-86 shown in Table 7 is used instead of Compound (I)-7. In this way, Electrophotographic photoreceptor-7 is obtained.

Example 18

Preparation of Electrophotographic Photoreceptor-8

The layers are formed up to the charge transport layer with the same preparation method as that of Electrophotographic photoreceptor-1, except that Compound (I)-111 shown in Table 8 is used instead of Compound (I)-7. In this way, Electrophotographic photoreceptor-8 is obtained.

Example 17

Preparation of Electrophotographic Photoreceptor-9

The layers are formed up to the charge transport layer with the same preparation method as that of Electrophotographic photoreceptor-1, except that Compound (E) represented by the following structural formula and a polymer having continuous Base units 2 below are used instead of Compound (D) and the polymer having continuous Base units 1. In this way, Electrophotographic photoreceptor-9 is obtained.

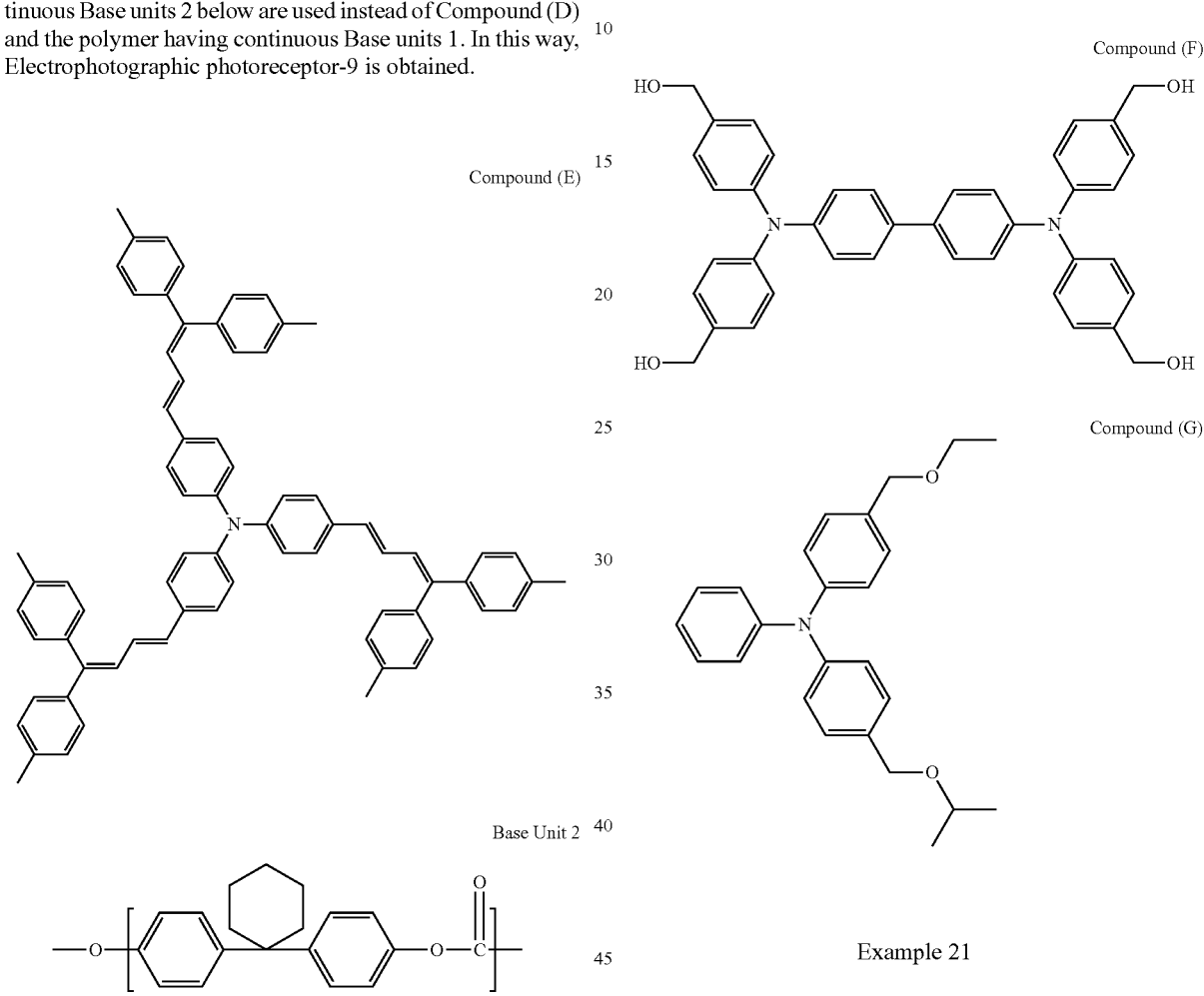

Example 20

Preparation of Electrophotographic Photoreceptor-10

The layers are formed up to the charge transport layer with the same preparation method as that of Electrophotographic photoreceptor-1, except that Compound (I)-7, LUBRON L-2 and GF-300 are not used.

0.5 part of Compound (I)-8 synthesized in Example 1, 3 parts of Compound (F) represented by the following structural formula, 0.4 part of Compound (G) represented by the following structural formula, 0.01 part of acid curing catalyst (NACURE 2500, manufactured by Kusumoto Chemicals, Ltd.), and 0.01 part of GF-400 (dispersing aid, manufactured by TOAGOSEI CO., LTD.) are dissolved in a mixed solution of 8 parts of cyclopentyl methyl ether and 2 parts of cyclopentanol. Then, 0.03 part of LUBRON L-2 is added thereto, followed by dispersion and mixing with a Nanomizer. As a result, a coating solution is obtained. This coating solution is coated on the obtained charge transport layer according to a ring-type dip coating method, followed by heating at 150° C. for 30 minutes to be cured. As a result, a surface protective layer with a thickness of 6 μm is formed. In this way, Electrophotographic photoreceptor-10 is obtained.

Example 21

Preparation of Electrophotographic Photoreceptor-11

The layers are formed up to the charge transport layer with the same preparation method as that of Electrophotographic Photoreceptor-10.

0.5 part of Compound (I)-7 synthesized in Example 2, 4 parts of Compound (H) represented by the following structural formula, 1 part of Compound (D), 1 part of the polymer having continuous Base units 2, 0.1 part of polymerization initiator (manufactured by Otsuka Chemical Co., Ltd., OTazo-15), 0.3 part of LUBRON L-2, and 0.01 part of CF-400 are dissolved in 6 parts of monochlorobenzene. As a result, a coating solution is obtained. This coating solution is spray-coated on the obtained charge transport layer and air-dried at room temperature for 1 hour, followed by heating at 155° C. for 45 minutes in a nitrogen atmosphere having an oxygen concentration of 200 ppm. As a result, a surface protective layer with a thickness of 8 μm is formed. In this way, Electrophotographic photoreceptor-11 is obtained.

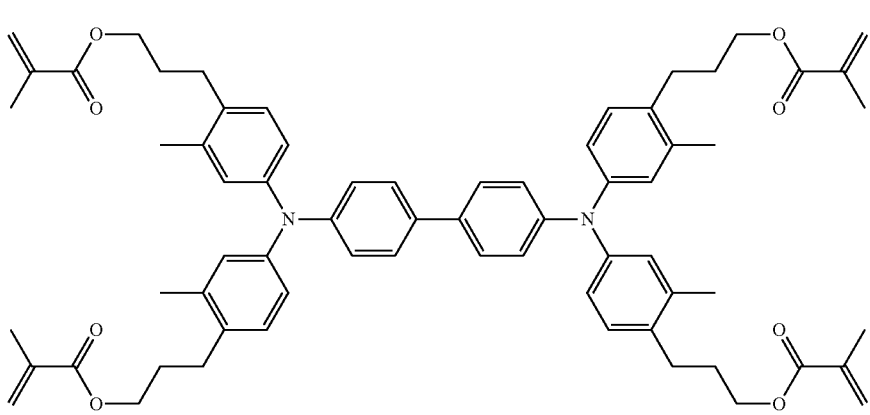

Compound (H)

Comparative Example 11

Preparation of Electrophotographic Photoreceptor-12

The layers are formed up to the charge transport layer with the same preparation method as that of Electrophotographic photoreceptor-1, except that Compound (I)-7 is not used and the amount of GF-300 is changed to 0.04 part. In this way, Electrophotographic photoreceptor-12 is obtained.

Comparative Example 12

Preparation of Electrophotographic Photoreceptor-13

The layers are formed up to the charge transport layer with the same preparation method as that of Electrophotographic photoreceptor-1, except that Compound (I)-7, LUBRON L-2, and GF-300 are not used. In this way, Electrophotographic photoreceptor-13 is obtained.

Comparative Example 13

Preparation of Electrophotographic Photoreceptor-14

The layers are formed up to the charge transport layer with the same preparation method as that of Electrophotographic photoreceptor-10, except that, when a surface protective layer is formed, Compound (I)-8 is not used and the amount of GF-400 is changed to 0.03 part. In this way, Electrophotographic photoreceptor-14 is obtained.

Comparative Example 14

Preparation of Electrophotographic Photoreceptor-15

The layers are formed up to the charge transport layer with the same preparation method as that of Electrophotographic photoreceptor-11, except that, when a surface protective layer is formed, Compound (I)-7 is not used and the amount of GF-400 is changed to 0.02 part. In this way, Electrophotographic photoreceptor-15 is obtained.

Comparative Example 15

Preparation of Electrophotographic Photoreceptor-16

The layers are formed up to the charge transport layer with the same preparation method as that of Electrophotographic photoreceptor-10, except that, when a surface protective layer is formed, Compound (I) represented by the following structural formula is used instead of Compound (I)-8 and the amount of GF-400 is changed to 0.03 part. In this way, Electrophotographic photoreceptor-16 is obtained.

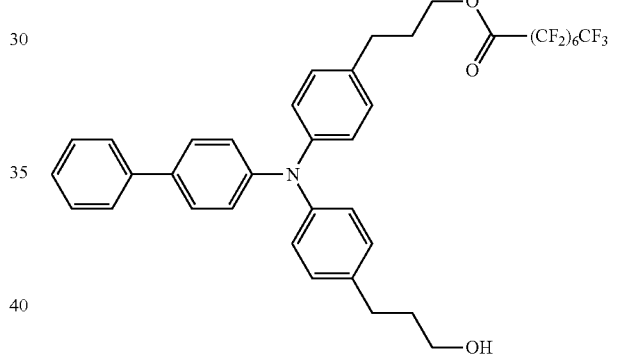

Compound (I)

Comparative Example 16

Preparation of Electrophotographic Photoreceptor-17

The layers are formed up to the charge transport layer with the same preparation method as that of Electrophotographic photoreceptor-11, except that, when a surface protective layer is formed, Compound (J) represented by the following structural formula which does not exhibit a charge transport property is used instead of Compound (I)-7 and the amount of GF-400 is changed to 0.05 part. In this way, Electrophotographic photoreceptor-17 is obtained.

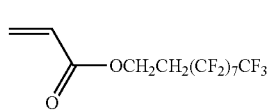

Compound (J)

Comparative Example 17

Preparation of Electrophotographic Photoreceptor-18

The layers are formed up to the charge transport layer with the same preparation method as that of Electrophotographic photoreceptor-10, except that, when a surface protective layer is formed, Compound (K) represented by the following structural formula is used instead of Compound (I)-8 and the amount of GF-400 is changed to 0.04 part. In this way, Electrophotographic photoreceptor-18 is obtained.

Compound (K)

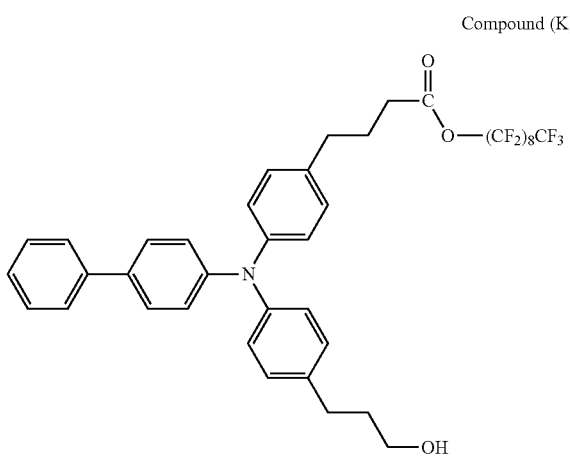

Comparative Example 18

Preparation of Electrophotographic Photoreceptor-19

The layers are formed up to the charge transport layer with the same preparation method as that of Electrophotographic photoreceptor-11, except that, when a surface protective layer is formed, Compound (L) represented by the following structural formula is used instead of Compound (I)-7 and the amount of GF-400 is changed to 0.05 part. In this way, Electrophotographic photoreceptor-19 is obtained.

Compound (L)

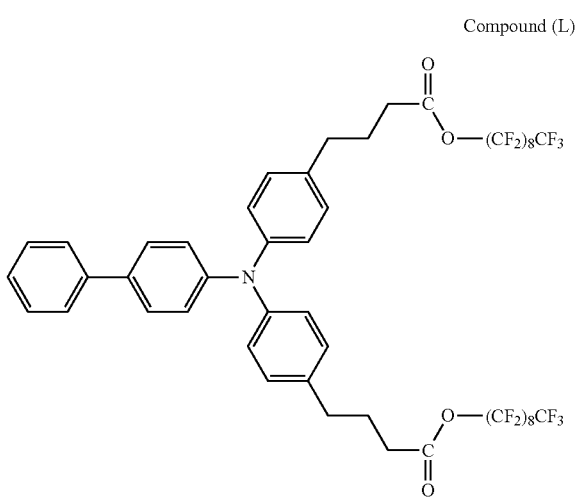

Evaluation

Electrophotographic photoreceptor-1 to Electrophotographic photoreceptor-19 obtained above are evaluated as follows. The results thereof are shown in Table 9.

Evaluation of Charging Stability

An image forming apparatus Color 1000 Press (manufactured by Fuji Xerox Co., Ltd.), to which any one of Electrophotographic photoreceptor-1 to Electrophotographic photoreceptor-19 is mounted, is prepared and a rate of forming an image is set to be a half. A cleaning blade is arranged in a direction opposite to a rotating direction of an electrophotographic photoreceptor under conditions of a contact angle of 23° and a contact load of 3 g/mm. A charging device is applied with a voltage such that the potential which is initially charged on the surface of an electrophotographic photoreceptor is −800 V, and the voltage applied at this time is maintained.

Using this image forming apparatus, 50,000 A4-sized images having a combined pattern of characters and patches are continuously formed on C2 paper (manufactured by Fuji Xerox Co., Ltd.) in an environment of 30° C. and 85% RH.

After forming the images, the potential (V) which is charged on the surface of an electrophotographic photoreceptor is measured using a potential probe. Then, using the difference ($\Delta$VH(V)) between the initially charged potential (−800 V) and a rising potential, the charging stability is determined according to the following criteria.

A: $\Delta$VH is less than 15 V
B: $\Delta$VH is greater than or equal to 15 V and less than 30 V
C: $\Delta$VH is greater than or equal to 30 V Other Evaluations Next, in an environment of 10° C. and 15% RH, 50,000 images are continuously formed in the same manner. The wear rate (nm/Kcycle) and the surface roughness (average Rz ($\mu$m) of surface roughnesses at ten points) of an electrophotographic photoreceptor are measured. In addition, whether or not there are attached materials such as contaminants attached to the surface of the electrophotographic photoreceptor due to toner or cured materials of toner and a photosensitive layer surface, are evaluated.

Next, in an environment of 30° C. and 85% RH, 50,000 images are continuously formed in the same manner. Then, half tone images (having an image density of 50%) are formed on the entire surface of paper. The cleaning property (image defects caused by cleaning failure of the attached materials), the transfer property, and the image quality (graininess) are evaluated.

The wear rate of an electrophotographic photoreceptor (nm/Kcycle) is obtained through a process in which the cross-section of an electrophotographic photoreceptor is observed through an electron microscope, the layer thickness thereof is measured to obtain a wear amount, and the obtained wear amount is normalized with the number of cycles (one rotation of the photoreceptor is set to one cycle) of the electrophotographic photoreceptor.

The surface roughness (average Rz ($\mu$m) of surface roughnesses at ten points) of an electrophotographic photoreceptor is measured using SURFCOM 1400A (manufactured by TOKYO SEIMITSU CO., LTD.) according to JISB 0601 (1994) under conditions of a cut-off length (standard length) of 0.8 mm and a measurement length of 4 mm.

Whether or not there are attached materials are determined according to the following criteria by visually inspecting the surface of an electrophotographic photoreceptor.

A: No attached materials are found
B: Attached materials are found in a portion of the area (30% or less of the area)

C: Attached materials are found in a wide range of the area (greater than 30% of the area)

The cleaning property is determined according to the following criteria by visually inspecting the half-tone images.
A: No image defects are found
B: Image defects such as streaks are found in a portion of the area (10% or less of the area).
C: Image defects such as streaks are found in a wide range of the area (greater than 10% of the area).

The transfer property is evaluated according to the amount of toner remaining on the surface of an electrophotographic photoreceptor after being transferred. Specifically, the toner remaining on the surface of an electrophotographic photoreceptor after being transferred is peeled off with an adhesive tape to measure the weight of the toner. The total cumulative weight of toner attached onto the surface of an electrophotographic photoreceptor is calculated as a percentage as transfer efficiency. This transfer efficiency is determined according to the following criteria.
A: The transfer efficiency is greater than or equal to 90%
B: The transfer efficiency is greater than or equal to 85% and less than 90%
C: The transfer efficiency is less than 85%

The image quality (graininess) is determined according to the following criteria by visually inspecting the half-tone images.
A: There is no graininess
B: There is graininess in a portion of the area (10% or less of the area)
C: There is graininess in a wide range of the area (greater than 10% of the area)

Accordingly, it can be seen that the additive for an electrophotographic photoreceptor represented by Formula (I) suppresses the change of the electrical characteristics of an electrophotographic photoreceptor and suppresses image defects during electrographic image formation.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An additive for an electrophotographic photoreceptor which is represented by Formula (I):

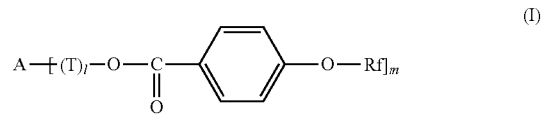

wherein in Formula (I), A represents an m-valent organic group derived from arylamine represented by Formula (II) or Formula (III); T represents a divalent hydrocarbon group having from 1 to 10 carbon atoms; Rf represents a branched hydrocarbon group having from 3 to 10 carbon atoms in which at least one hydrogen atom is substituted with a fluorine atom; l represents 0 or 1; and m represents an integer of 1 to 4:

TABLE 9

| | Electrophotographic Photoreceptor | Presence of Surface Protective Layer | Outermost Surface Layer Compound | Addition of Fluororesin Particles | Charging Stability | Wear Rate (nm/Kcycle) | Surface Roughness Rz (μm) | Attachment | Cleaning Property | Transfer Property | Image Quality (Graininess) |
|---|---|---|---|---|---|---|---|---|---|---|---|
| Example 11 | 1 | — | (I)-7 | Added | A | 13 | 2.2 | A | A | A | A |
| Example 12 | 2 | — | (I)-7 | — | A | 15 | 1.8 | A | A | A | A |
| Example 13 | 3 | — | (I)-10 | Added | A | 9 | 2.3 | A | A | A | A |
| Example 14 | 4 | — | (I)-11 | Added | A | 10 | 2.4 | A | A | A | A |
| Example 15 | 5 | — | (I)-27 | Added | A | 12 | 2.0 | A | A | A | A |
| Example 16 | 6 | — | (I)-65 | Added | A | 12 | 1.9 | A | A | A | A |
| Example 17 | 7 | — | (I)-86 | Added | A | 14 | 2.2 | A | A | A | A |
| Example 18 | 8 | — | (I)-111 | Added | A | 10 | 2.1 | A | A | A | A |
| Example 19 | 9 | — | (I)-7 | Added | A | 12 | 2.2 | A | A | A | A |
| Example 20 | 10 | Present | (I)-8 | Added | A | 3.4 | 0.6 | A | A | A | A |
| Example 21 | 11 | Present | (I)-7 | Added | A | 2.1 | 0.4 | A | A | A | A |
| Comparative Example 11 | 12 | — | — | Added | C | 15 | 2.8 | A | B | B | B |
| Comparative Example 12 | 13 | — | — | — | B | 21 | 2.5 | C | C | B | B |
| Comparative Example 13 | 14 | Present | — | Added | C | 3.8 | 0.8 | B | B | B | B |
| Comparative Example 14 | 15 | Present | — | Added | C | 2.4 | 0.9 | B | B | B | B |
| Comparative Example 15 | 16 | Present | Compound (I) | Added | C | 6 | 1.1 | C | B | B | B |
| Comparative Example 16 | 17 | Present | Compound (J) | Added | C | 4.1 | 1.0 | C | B | B | B |
| Comparative Example 17 | 18 | Present | Compound (K) | Added | C | 4.5 | 1.1 | C | B | B | B |
| Comparative Example 18 | 19 | Present | Compound (L) | Added | C | 4.9 | 1.0 | C | B | B | B |

It can be seen from the results shown in Table 9 that, when the electrophotographic photoreceptors of Examples 11 to 21 are compared to those of Comparative Examples 11 to 18, the change in electrical characteristics is suppressed and image defects are suppressed during image formation.

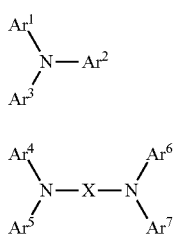
(II)

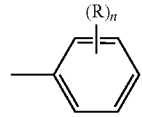
(III)

wherein in Formula (II), Ar¹, Ar², and Ar³ each independently represent a substituted or unsubstituted aryl group having from 6 to 20 carbon atoms; in Formula (III), Ar⁴, Ar⁵, Ar⁶, and Ar⁷ each independently represent a substituted or unsubstituted aryl group having from 6 to 20 carbon atoms; and X represents a divalent organic group represented by Formula (IV), Formula (V), or Formula (VI):

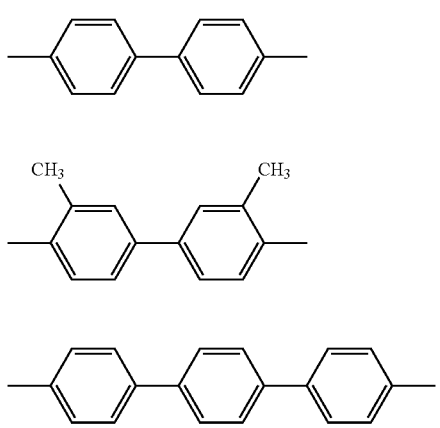

(IV)

(V)

(VI)

2. The additive for an electrophotographic photoreceptor according to claim 1,
wherein, in Formula (I), Rf represents a hydrocarbon group having two or more branched chains.

3. The additive for an electrophotographic photoreceptor according to claim 1,
wherein, in Formula (II) and Formula (III), the substituted or unsubstituted aryl groups having from 6 to 20 carbon atoms which are represented by Ar¹, Ar², Ar³ Ar⁴, Ar⁵, Ar⁶, and Ar⁷ are aryl groups represented by the following formulae:

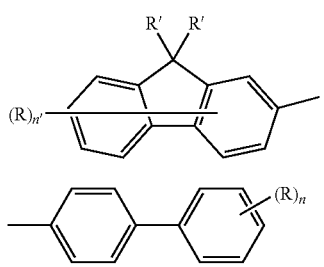

(Ar-1)

(Ar-2)

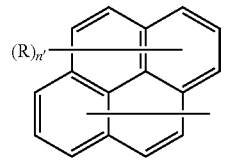
(Ar-3)

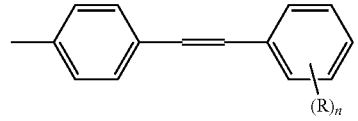
(Ar-4)

(Ar-5)

(Ar-6)

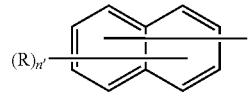

wherein, R and R' each independently represent a halogen atom, a substituted or unsubstituted alkyl group having from 1 to 5 carbon atoms, a substituted or unsubstituted alkoxy group having from 1 to 5 carbon atoms, a substituted or unsubstituted hydroxyalkyl group having from 1 to 5 carbon atoms, a substituted or unsubstituted alkenyl group having from 2 to 5 carbon atoms, or a substituted or unsubstituted aryl group having from 6 to 14 carbon atoms; n represents an integer of 0 to 5; and n' represents an integer of 0 to 7.

4. The additive for an electrophotographic photoreceptor according to claim 1,
wherein the compound represented by Formula (II) is a compound represented by Formula (II-1):

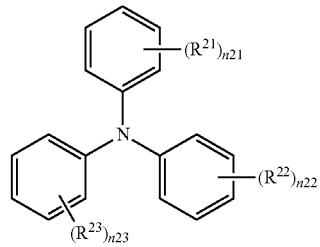
(II-1)

wherein in Formula (II-1), $R^{21}$, $R^{22}$, and $R^{23}$ each independently represent a halogen atom, a substituted or unsubstituted alkyl group having from 1 to 5 carbon atoms, a substituted or unsubstituted alkoxy group having from 1 to 5 carbon atoms, a substituted or unsubstituted hydroxyalkyl group having from 1 to 5 carbon atoms, a substituted or unsubstituted alkenyl group having from 2 to 5 carbon atoms, or a substituted or unsubstituted aryl group having from 6 to 14 carbon atoms; and n21, n22, and n23 each independently represent an integer of 0 to 5.

5. The additive for an electrophotographic photoreceptor according to claim 1,
wherein the compound represented by Formula (II) is a compound represented by Formula (III-1):

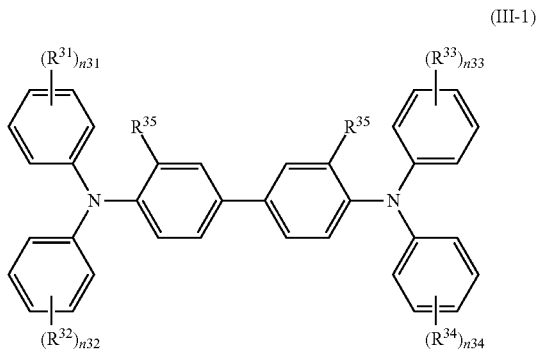

(III-1)

wherein in Formula (III-1), $R^{31}$, $R^{32}$, $R^{33}$, and $R^{34}$ each independently represent a halogen atom, a substituted or unsubstituted alkyl group having from 1 to 5 carbon atoms, a substituted or unsubstituted alkoxy group having from 1 to 5 carbon atoms, a substituted or unsubstituted hydroxyalkyl group having from 1 to 5 carbon atoms, a substituted or unsubstituted alkenyl group having from 2 to 5 carbon atoms, or a substituted or unsubstituted aryl group having from 6 to 14 carbon atoms; n31, n32, n33, and n34 each independently represent an integer of 0 to 5; and $R^{35}$ represents a hydrogen atom or a methyl group.

6. An electrophotographic photoreceptor comprising:
a conductive substrate; and
a photosensitive layer that is provided on the conductive substrate,
and an outermost surface layer of the electrophotographic photoreceptor is a layer formed of a composition which includes a charge transport material, fluororesin particles, and the additive for an electrophotographic photoreceptor according to claim 1.

7. The electrophotographic photoreceptor according to claim 6,
wherein the additive for an electrophotographic photoreceptor is represented by Formula (I) in which Rf represents a hydrocarbon group having two or more branched chains.

8. An electrophotographic photoreceptor comprising:
a conductive substrate; and
a photosensitive layer that is provided on the conductive substrate,
and an outermost surface layer of the electrophotographic photoreceptor is a layer formed of a composition which includes a charge transport material, fluororesin particles, and the additive for an electrophotographic photoreceptor according to claim 3.

9. An electrophotographic photoreceptor comprising:
a conductive substrate; and
a photosensitive layer that is provided on the conductive substrate,
and an outermost surface layer of the electrophotographic photoreceptor is a layer formed of a composition which includes a charge transport material, fluororesin particles, and the additive for an electrophotographic photoreceptor according to claim 4.

10. An electrophotographic photoreceptor comprising:
a conductive substrate; and
a photosensitive layer that is provided on the conductive substrate,
and an outermost surface layer of the electrophotographic photoreceptor is a layer formed of a composition which includes a charge transport material, fluororesin particles, and the additive for an electrophotographic photoreceptor according to claim 5.

11. The electrophotographic photoreceptor according to claim 6,
wherein a content of the fluororesin particles is from 1% by weight to 30% by weight with respect to all of the components of the outermost surface layer (in terms of solid content).

12. The electrophotographic photoreceptor according to claim 6,
wherein an average primary particle size of the fluororesin particles is from 0.01 μm to 10 μm.

13. The electrophotographic photoreceptor according to claim 6,
wherein the fluororesin is selected from a group consisting of polytetrafluoroethylene, perfluoroalkoxy fluororesin, polychlorotrifluoroethylene, polyvinylidene fluoride, polydichlorodifluoroethylene, tetrafluoroethylene-perfluoroalkylvinylether copolymer, tetrafluoroethylene-hexafluoropropylene copolymer, tetrafluoroethylene-ethylene copolymer, and tetrafluoroethylene-hexafluoropropylene-perfluoroalkylvinylether copolymer.

14. An image forming apparatus comprising:
an electrophotographic photoreceptor;
a charging unit that charges a surface of the electrophotographic photoreceptor with electricity;
a latent image forming unit that forms an electrostatic latent image on a charged surface of the electrophotographic photoreceptor;
a developing unit that develops the electrostatic latent image, which is formed on the surface of the electrophotographic photoreceptor, using a toner to form a toner image; and
a transfer unit that transfers the toner image, which is formed on the surface of the electrophotographic photoreceptor, onto a recording medium,
wherein the electrophotographic photoreceptor is the electrophotographic photoreceptor according to claim 6.

15. The image forming apparatus according to claim 14,
wherein the additive for an electrophotographic photoreceptor is represented by Formula (I) in which Rf represents a hydrocarbon group having two or more branched chains.

16. A process cartridge comprising:
an electrophotographic photoreceptor; and
a cleaning unit that cleans the electrophotographic photoreceptor,
wherein the electrophotographic photoreceptor is the electrophotographic photoreceptor according to claim 6.

17. The process cartridge according to claim 16,
wherein the additive for an electrophotographic photoreceptor is represented by Formula (I) in which Rf represents a hydrocarbon group having two or more branched chains.

* * * * *